US012419704B2

(12) United States Patent
Stefanini et al.

(10) Patent No.: US 12,419,704 B2
(45) Date of Patent: Sep. 23, 2025

(54) CONCENTRIC TUBE ROBOTS WITH IMPROVED STABILITY FOR MINIMALLY INVASIVE SURGERY

(71) Applicant: Khalifa University of Science and Technology, Abu Dhabi (AE)

(72) Inventors: Cesare Stefanini, Abu Dhabi (AE); Hessa Al Falahi, Abu Dhabi (AE); Federico Renda, Abu Dhabi (AE)

(73) Assignee: Khalifa University of Science and Technology, Abu Dhabi (AE)

( * ) Notice: Subject to any disclaimer, the term of this patent is extended or adjusted under 35 U.S.C. 154(b) by 512 days.

(21) Appl. No.: 17/998,007

(22) PCT Filed: May 19, 2021

(86) PCT No.: PCT/IB2021/054335
§ 371 (c)(1),
(2) Date: Nov. 4, 2022

(87) PCT Pub. No.: WO2021/234604
PCT Pub. Date: Nov. 25, 2021

(65) Prior Publication Data
US 2023/0165646 A1 Jun. 1, 2023

Related U.S. Application Data

(60) Provisional application No. 63/027,908, filed on May 20, 2020.

(51) Int. Cl.
*A61B 34/30* (2016.01)
*A61B 18/14* (2006.01)
(Continued)

(52) U.S. Cl.
CPC .... *A61B 34/30* (2016.02); *A61B 2017/00305* (2013.01); *A61B 2017/00318* (2013.01); *A61B 2034/301* (2016.02); *A61M 25/0113* (2013.01)

(58) Field of Classification Search
CPC ...... A61B 18/1492; A61B 2017/00305; A61B 2017/00314; A61B 2017/00318;
(Continued)

(56) References Cited

U.S. PATENT DOCUMENTS

2011/0270172 A1 11/2011 Selkee
2012/0209293 A1 8/2012 Carlson et al.
(Continued)

FOREIGN PATENT DOCUMENTS

| JP | 2015198940 A | 11/2015 |
| KR | 20150082243 A | 7/2015 |
| KR | 20180038070 A | 4/2018 |

OTHER PUBLICATIONS

Application No. PCT/IB2021/054335, International Search Report and Written Opinion, Mailed On Aug. 23, 2021, 12 pages.

*Primary Examiner* — Scott Luan
(74) *Attorney, Agent, or Firm* — Kilpatrick Townsend & Stockton LLP

(57) ABSTRACT

A robotic catheter can include bi-stable concentric tubes and a torsional spring mechanism that can provide torque at the proximal extremity of one or more tubes. The robotic catheter can compensate for the energy that may be released by the tubes snapping from on stable-equilibrium position to another by using the energy stored in the torsional spring mechanism. The energy released by the tubes upon snapping from one stable-equilibrium position to the other can be compensated by the energy stored in the torsional spring at the base, thereby resulting in the first, energy-free, zero stiffness catheter system that (1) synchronizes with the motion of the heart and (2) naturally results in optimal, pseudo-constant contact force with the tissue.

15 Claims, 18 Drawing Sheets

(51) Int. Cl.
   *A61B 17/00*     (2006.01)
   *A61M 25/01*     (2006.01)
(58) Field of Classification Search
   CPC ........... A61B 2017/00725; A61B 2018/00351;
           A61B 2018/00577; A61B 2034/301;
           A61B 2034/302; A61B 34/30; A61M
             2025/0004; A61M 25/0082; A61M
         25/0105; A61M 25/0113; A61M 25/0158
   See application file for complete search history.

(56) References Cited

U.S. PATENT DOCUMENTS

| | | |
|---|---|---|
| 2013/0165754 A1 | 6/2013 | Frassica et al. |
| 2017/0202616 A1 | 7/2017 | Pate et al. |

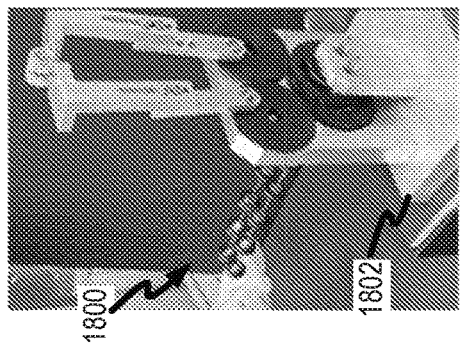
FIG. 18A  FIG. 18B  FIG. 18C
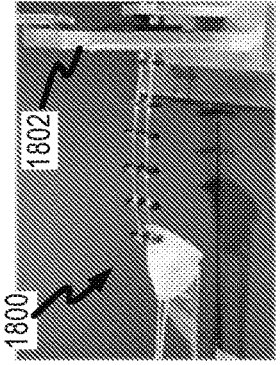
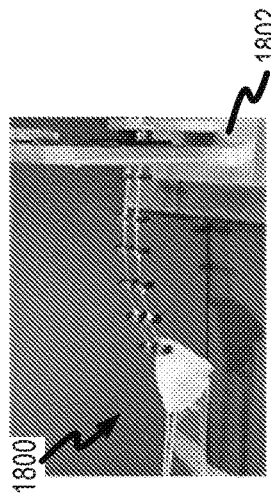
FIG. 18D  FIG. 18E  FIG. 18F
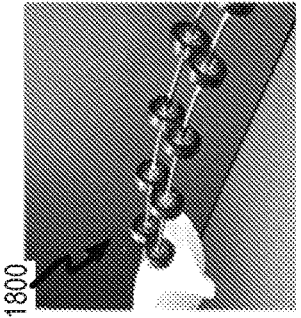
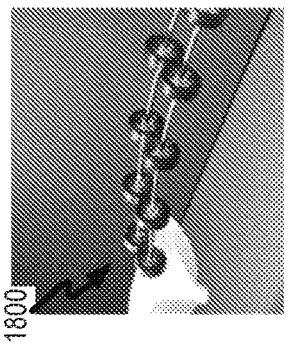
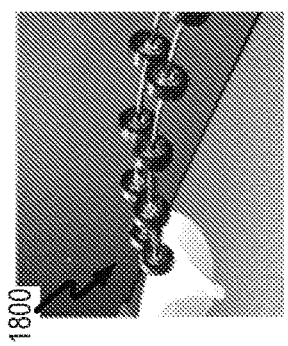
FIG. 18G  FIG. 18H  FIG. 18I

CONCENTRIC TUBE ROBOTS WITH IMPROVED STABILITY FOR MINIMALLY INVASIVE SURGERY

BACKGROUND

Minimally invasive technologies in cardiac surgery mitigated the significant intra-operative surgical trauma to which the patients are exposed during the traditional open-heart surgery, also referred to as median sternotomy. Using catheters and guidewires through small incisions, Minimally Invasive Cardiac Surgery (MICS) results in reduced post-operative complications and wound infections, better cosmetic results and faster recovery. MICS ameliorates the state-of-the-art of heart surgery not only by eliminating the need for long chest incisions, but also allowing the performance on the beating heart, thereby precluding the use of cardiopulmonary bypass. Despite their advantages, the currently available catheters used in MICS generally provide limited haptic feedback, insufficient intra-operative force on the beating tissue, or poor localization due to their inability to track the rapid motion of the beating heart. This results in reduced success rate of MICS and also impose the need for repeat surgeries (e.g., contact disturbance, detachment and blood heating, or even tissue perforation).

The aforementioned challenge of beating heart minimally invasive surgery, which is the inability of existing catheters to apply optimal, constant force on the beating tissue is particularly reflected on the low success rate of cardiac ablation, a procedure performed to treat arrhythmia patients, whose hearts beat either faster or slower than normal. This is because the efficacy of the procedure depends on the efficient energy delivery through an electrode at the tip of the catheter, this energy is delivered in the form of an electric current to denature the diseased tissue and transform it into scar tissue, thereby restoring the normal heart rhythm. Due to the rapid movement of the heart, the contact force between the catheter tip and the tissue is usually not constant, precluding complete blockage of the target surgical sites, resulting in arrhythmia recurrence. This contact disturbance not only reduces the quality of the procedure, but also leads to surgical complications, such as blood heating and coagulation, which happens due to the detachment of the tip electrode from the tissue and the exposure of the circulating blood to heat. An important surgical requirement is also to ensure that the force is not lower than 0.1 N, which is considered insufficient, and also not to exceed 0.4 N, above which the excessive forces can cause tissue perforation.

The dilemma of contact force control in beating heart surgery or MICS has been tackled in literature mainly by incorporating haptic feedback systems and their sensory data during image-guided surgeries. However, systems that depend on real-time imaging for surgical guidance suffer from time delays that result from the image acquisition and processing, rendering such control architectures divergent and therefore unreliable. Additionally, miniaturized force sensors impose several questions regarding sterilization, electromagnetic compatibility, MRI compatibility and the general mechanical properties of the catheter. Therefore, improved robotic systems for minimally invasive cardiac surgery are desired.

BRIEF SUMMARY

Embodiments described herein include a passively controlled robotic cardiac catheter that can interact with moving heart tissue during cardiac ablation. The robotic catheter can synchronize with the motion of the heart and naturally results in pseudo-constant tip contact force at the prescribed value compatible with surgical requirements mentioned earlier. Having constant or pseudo-constant contact force with the tissue can reduce the risks of surgical injury by precluding the need for repetitive manual manipulation of the catheter. The passive control can also reduce surgical time by reducing or eliminating the need for computationally inefficient control architectures that depend on predictive filters to compensate for the heart motion. Additionally, by not requiring force sensors for active monitoring, passively controlled robotic catheters can be formed using materials that are MRI-compatible and can be miniaturized, and in the same time, they do not require clinicians' training, and are ergonomically suitable.

The aim of the robotic catheter described here is to establish a paradigm shift toward passive, natural force control, without the need for active control systems that depend on sensors and are characterized with computational complexity for tracking and predicting the motion of the heart. The system described here is the first passively controlled robotic catheter designed for beating heart surgery and in particular, cardiac ablation. The robotic catheter can include a statically-balanced compliant mechanism composed of distal bi-stable concentric tubes and a compliant torsional spring mechanism that can provide torque at tube proximal extremity, resulting in an energy-free catheter with a zero-stiffness tip. The robotic catheter can maintain surgical efficacy and safety despite the chaotic displacement of the heart, by naturally keeping the tip force at an optimal level, not less and not more than the surgical requirement.

In various embodiments, the robotic catheter can be a concentric tube robotic-catheter that includes distal bi-stable concentric tubes concentrically arranged and a torsional spring mechanism connected to the proximal end of the concentric tubes via a geared mechanism, resulting in a statically balanced catheter tip with constant force. The concentric tubes can snap between two stable equilibrium positions when they are counter-rotated and the torsional spring mechanism can compensate for the energy released by the concentric tubes snapping between the two stable equilibrium positions by using energy stored in the torsional spring mechanism to cause the concentric tubes to counter-rotate relative to one another. The counter-rotation can cause bending of the concentric tubes that allows the tip of the concentric tubes to maintain a pseudo-constant contact force with tissue as it moves, for example, moving heart tissue.

BRIEF DESCRIPTION OF THE DRAWINGS

FIGS. 18A through 18I show a concentric tube robot, according to various embodiments.

DETAILED DESCRIPTION

Figure 1:
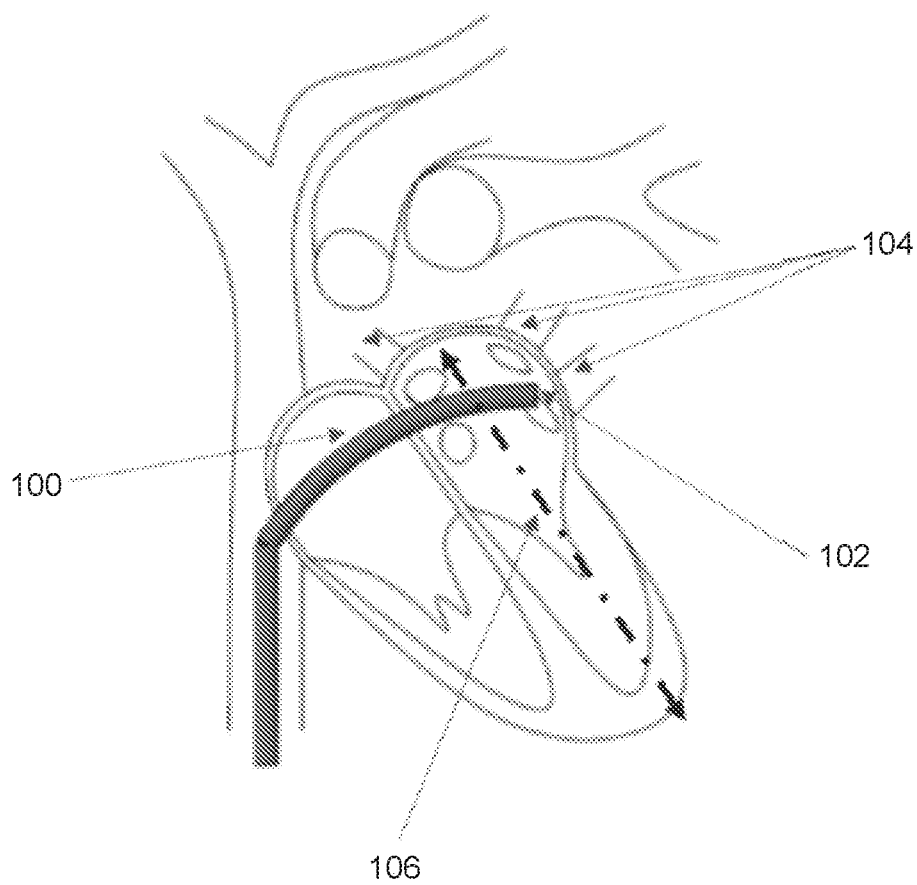
FIG. 1 shows a known catheter inserted into a heart.

In the following description, various embodiments will be described. For purposes of explanation, specific configurations and details are set forth in order to provide a thorough understanding of the embodiments. However, it will also be apparent to one skilled in the art that the embodiments may be practiced in other configurations, or without the specific details. Furthermore, well-known features may be omitted or simplified in order not to obscure the embodiment being described.

Cardiac ablation is a procedure that can be used for treating arrhythmia in some cardiac patients. Arrhythmia can be caused when some accessory pathways within the heart initiate premature electrical signals that result in irregular contractions. During a cardiac ablation procedure, diseased areas associated with arrhythmia-causing pathways are exposed to radiofrequency energy to be transformed into scar tissue, thereby reducing the initiation of premature electrical signaling and restoring a normal heart rhythm.

Minimally Invasive Cardiac Surgery (MICS) ameliorates the state-of-the-art of heart surgery not only by eliminating the need for long chest incisions, but also allowing the performance on the beating heart. Although MICS is a major convenience for patients, it imposes several challenges from the physicians' point-of-view. Among these challenges are the loss of haptic feedback, as well as the difficulty in achieving consistent, and sufficient mechanical interaction with the tissue, which is mainly attributed to the inherent flexibility of cardiac catheters and the rapid motion of the heart. The beating motion of the heart exceeds the tracking frequency of human bandwidth, therefore renders the manual manipulation of the catheters unreliable and ineffective. The challenge of attaining a constant, optimal contact force on the beating tissue is particularly reflected on the compromised efficacy of cardiac radiofrequency ablation, hence, we dedicate our work to this procedure which can be performed to treat drug-resistive arrhythmia patients, those suffering from irregular heart contractions, either faster or slower than the normal rate.

One of the most common types of arrhythmia especially in the elderly population, is Atrial Fibrillation (AF), in which the atria contracts faster than normal. AF is characterized by chaotic contractions of the atria, and is associated with high risk of arterial thromboembolic events and ischemic stroke.

Drug resistive AF patients are cured using catheter ablation of the Pulmonary Veins, which have been shown to be the most common source that triggers the impaired electrical signals resulting in AF. This ablation procedure is called Pulmonary Vein Isolation (PVI), during which the pulmonary veins in the left atrium are circumferentially ablated.

Embodiments described herein relate generally to robotic catheters that utilize concentric tubes to apply a pseudo-constant force on moving tissue using the tip of the concentric tubes. The concentric tubes can be counter rotated relative to one another using a spring mechanism connected to the concentric tubes to compensate for energy dissipated when the concentric tubes move between the two stable positions. The robotic catheters described herein can be used in, e.g., cardiac ablation procedures, mitral valve replacement and/or repair, pacemaker implantation, coronary artery bypass, minimally invasive beating heart surgery or other suitable procedures in which catheters having the ability to track the high speed of the moving cardiac tissue when manually manipulated and achieve mechanical interaction can be used.

FIG. 1 shows a known ablation catheter 100 with an electrode tip 102 which delivers radio frequency energy to the entries of the pulmonary veins 104 in a circumferential manner. This energy causes the transformation of the diseased tissue into scar tissue, thereby restoring the normal heart rhythm. However, the pulmonary veins 104 usually reconnect after surgery with a high probability of AF recurrence (20%-55%). This is primarily attributed to the failure of existing ablation catheters to form transmural lesions that penetrate the whole thickness of endocardium. This happens due to contact disturbance, where the catheter detaches from the tissue during cardiac diastole, and consistent contact become technically not possible with manual manipulation, leading to inefficient energy deliver to the target sites, and incomplete blockage. Although complete blockage of the target areas is usually attained at the end of the procedure, the blocked pathways usually reconnect a few months after the surgery in up to 70% of patients. The robotic catheter described herein is capable of maintaining a consistent, optimal contact force despite the motion of the heart tissue. This motion can be dominant along the mitral valve axis 106. The average motion along this axis can be between 8 mm and 15 mm. Accordingly, a 1 degree of freedom catheter tip is sufficient to follow the movement of the left atrial wall.

Some know catheters can provide real-time force feedback during ablation, and hence improved the procedure outcome. Despite the undeniable improvement of beating heart surgery by incorporating force sensors and feedback systems. However, these known system still have challenges and limitations. For example, miniaturized force sensors impose several questions regarding sterilization and measurement accuracy. The friction between the catheter and the insertion point, as well as the friction with the wall vessels can distort the distal force measurements. The force sensors can also increase the stiffness and alter the mechanical properties of the catheter tip. In contrast, the robotic catheters described herein, can include catheter tips that can naturally maintain constant, optimal contact force with beating heart tissue.

Figure 2:
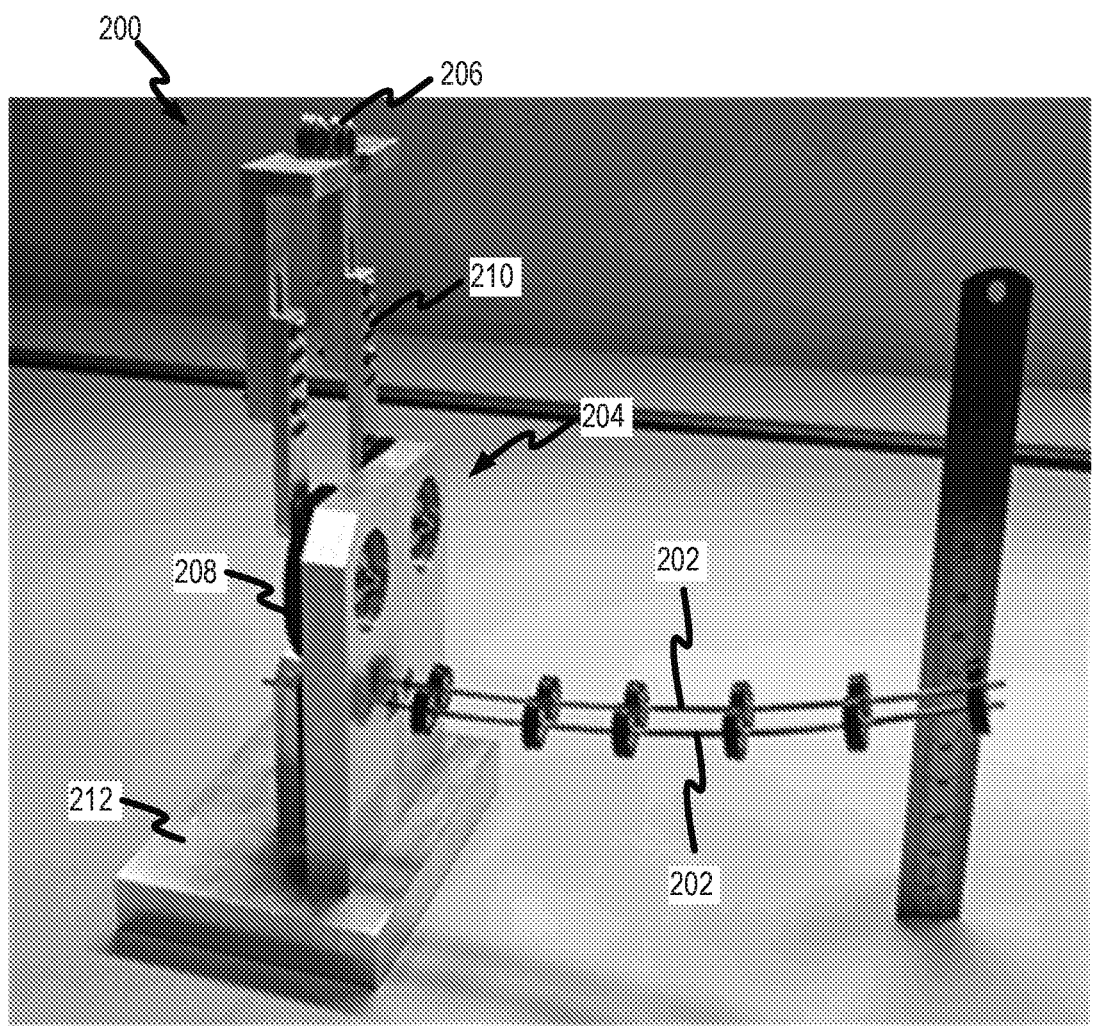
FIG. 2 shows a robotic catheter that utilizes two eccentric tubes, in accordance with various embodiments.

FIG. 2 shows a robotic catheter 200 including tubes 202 (e.g., tubes arranged concentrically and/or eccentrically), in accordance with various embodiments. The robotic catheter 200 can be passively or semi-passively controlled during cardiac ablation procedure. For example, the robotic catheter 200 can be controlled using a design-based control, (e.g., by applying a constant or semi-constant force to the moving tissue with the tip). The robotic catheter 200 can be used without needing input from real-time control or sensors to properly function. The passive robotic catheter can produce a desired, consistent contact force with the tissue, precluding the need for the repetitive manual manipulation of the catheter, and significantly reducing the risks of surgical injury. The passive robotic catheter may also reduce the surgical time by reducing or eliminating the need for computationally inefficient control architectures that depend on predictive filters of heart motion. Having a catheter that can operate without sensors, the catheter can be MRI-compatible and even more miniaturized. In various embodiments, the robotic catheter can include concentric tube robots of highly mechanical robustness that can be used to target intraoperative force control.

The robotic catheter 200 can include tubes 202 arranged eccentrically (as shown) or arranged concentrically. For example, the arrangement of the tubes 202 may have a minimal, if any, effect on the use of the robotic catheter 200. For example, the arrangement of the tubes 202 may be the same except for the tubes being separated by an offset distance when eccentrically arranged. In the eccentric arrangement, the friction between the tubes can be reduced or eliminated compared with the concentric arrangement and/or the two outer tubes can have the same or similar torsional stiffness without the need for further machining. In various embodiments, the eccentric arrangement can be converted to the concentric arrangement. The tubes 202 can be attached to a spring mechanism 204 that includes a spring 206 connected to gears 208 via L-shaped links 210. Multiple gears 208 can be coupled with a base 212. For example, in various embodiments, four gears 208 can be coupled with the base 212. The gears 208 can include two upper driving gears that transmits torque to two lower driven gears. The gears 208 may vary in dimensions or may have the same or similar dimensions. For example, the gears 208 may have a radii of 21.45 mm and thickness of 3 mm. The gears 208 may be machined, for example, the upper driving gears may be machined, creating room for the adjacent tube upon counter-rotation. The gears 208 can be connected to the tubes 202 and mounted the base 212. The base 212 can be or include metal, for example, Aluminum Series 6000. The lower driven gears 208 can facilitate the counter-rotation of the tubes 202 relative to one another in response to the tubes 202 snapping between positions, causing a torque around the center of the spring 206, which in turn results in a deflection angle of the tubes.

Figure 3A:
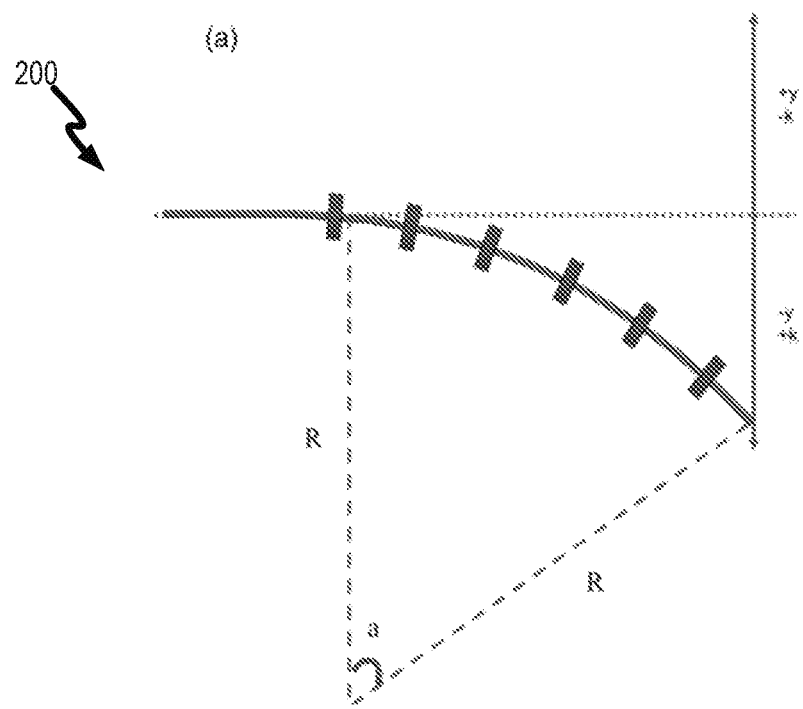
FIGS. 3A and 3B illustrate movement of the robotic catheter of FIG. 2, in accordance with various embodiments.
Figure 3B:
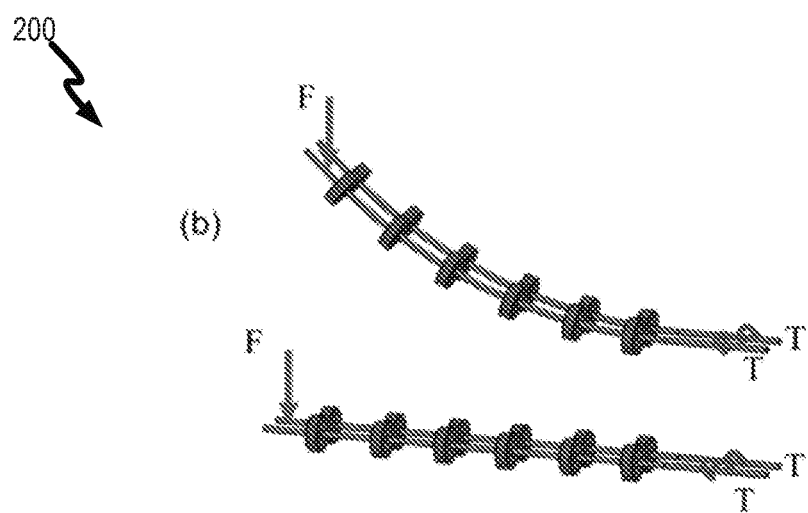

FIGS. 3A and 3B show the example robotic catheter 200 at various positions. FIG. 3A shows a two-dimensional, lateral representation of robotic catheter 200 with an initial curvature of θ=0°. FIG. 3B shows a three-dimensional free body diagram of the example robotic catheter 200, with various forces acting on it. The forces including a distal vertical force at the tip and a distal torque counter-rotating the tubes at the base. FIG. 3B shows the robotic catheter 200 curved up, straightened, and curved down.

Figure 4:
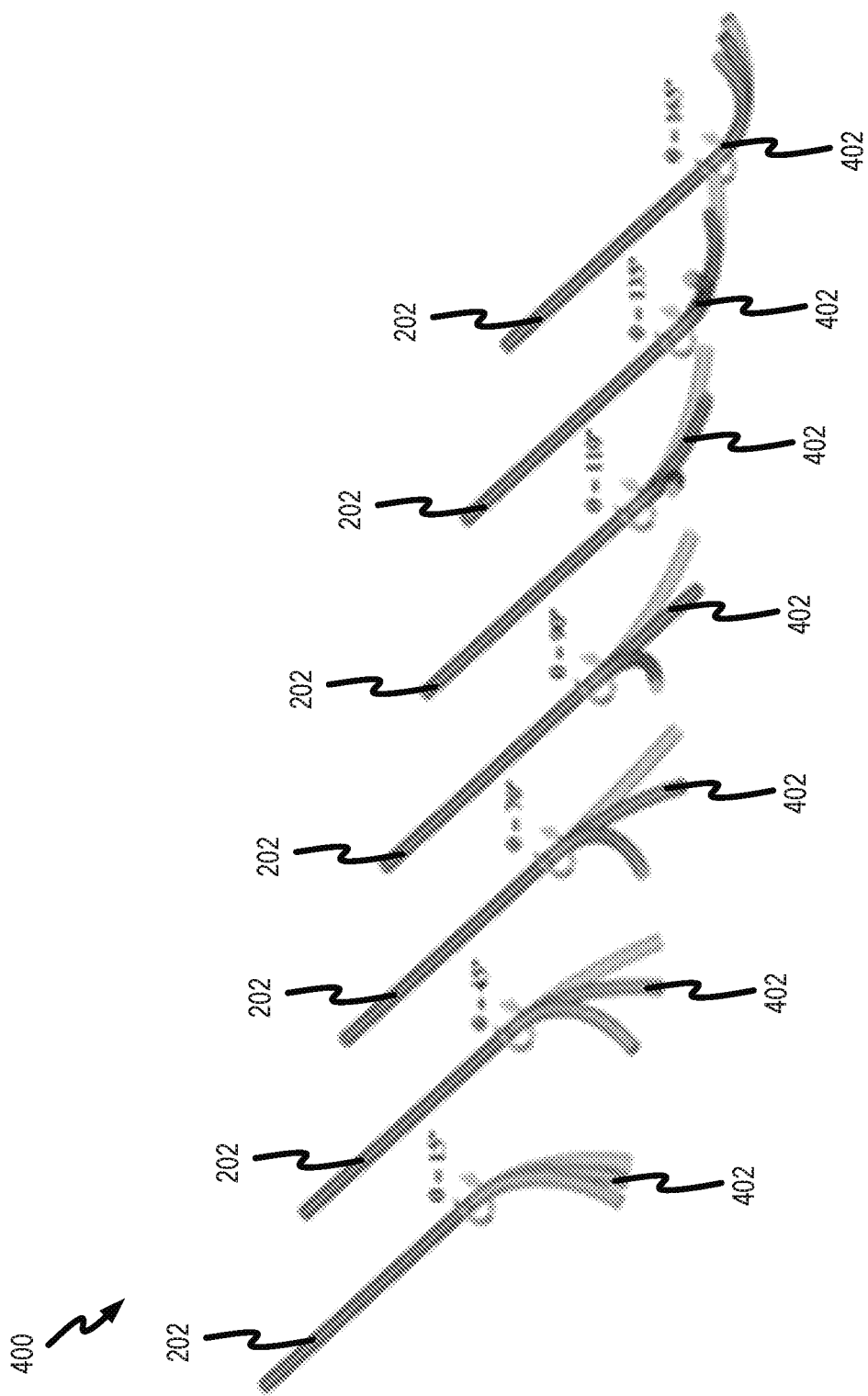
FIG. 4 shows a bi-stable concentric tube robot employing two bi-stable concentric tubes, illustrating movement of the bi-stable concentric tubes, in accordance with various embodiments.

FIG. 4 shows a distal end of a bi-stable tube robot 400. The bi-stable tube robot 400 can be or include the robotic catheter 200. The bi-stable tube robot 400 can include two tubes 202 moving between positions, in accordance with various embodiments. The bi-stable tube robot 400 can be or include an eccentric and/or concentric tube robot. The distal end of the bi-stable tube robot 400 can interact with the beating heart during minimally invasive cardiac ablation. The bi-stable tube robot 400 can be used with path planning, which can aid in the bi-stable tube robot 400 avoiding collision with delicate tissues and proper position control of the manipulators. In some embodiments, the bi-stable tube robot 400 can be image-guided using fluoroscopy. The tubes 202 can be or include compliant tubes that deform by bending and twisting when relatively rotated and translated at their bases. Unlike steerable needles, the elastic interaction between the tubes 202 generates the steering force, what makes them capable of navigating through hollow and liquid-filled cavities. The tubes 202 can be made of (super) elastic tubes nested one inside the other. The continuous deformation (bending and torsion) along the robot backbone, as a result of the rotation of the tubes 202 and translation at their base, makes them suitable for navigation through the complex, tortuous body lumens like blood vessels and brain ventricles. Moreover, the geometrical and mechanical models developed for the bi-stable tube robot 400 can be deployed to achieve surgery- and patient-specific tip position, force and stiffness control, thereby resulting in better mechanical interaction with the surgical site. Due to their controllable mechanical characteristics, concentric tube robots have been adopted as minimally invasive surgical manipulators. In various embodiments, the bi-stable tube robot 400 can be or include a distal catheter. In further embodiments, the bi-stable tube robot 400 can include eccentric or concentric tubes.

A. Instability Exploitation

The high bending stiffness of the bi-stable tube robot 400, especially those made from tubes 202 that have been highly curved, make the tubes twist rather than bend, when they are relatively rotated, The tubes 202, as a result, suddenly release the stored energy and snap to a lower energy configuration. This phenomenon can be referred to as instability or perturbation, and can be usually avoided due to potential risks of injury if happens during surgical intervention. This phenomenon has been always avoided, except in, (e.g., instances where that snapping of the tubes from one angle to another can be exploited to drive a robotic needle into the tissue, while minimizing Cartesian tip motion). The instability that results from the counter-rotation of two tubes can be used to compensate for the motion of the heart.

B. Stiffness Balance

A statically-balanced stiffness can be made by amalgamating two types of compliant mechanisms in the catheter system: (1) an arrangement of bi-stable concentric tubes, arranged in an outer sheath, can snap between two stable equilibrium positions and (2) a spring mechanism attached via gears that provide the torque necessary to counter-rotate the tubes 202. For example, the torque can counter-rotate the two outermost tubes. A mechanism, in which the energy released by the tubes when snapping between the two stable configurations can be compensated by the energy stored in the spring, can result in an overall compliant system of zero-stiffness, energy free tip motion. This can be the first stiffness balancing mechanism applied on concentric tube robots for passive force control in minimally invasive surgery. A quasi-static mathematical model of the concentric tube robot can be used to evaluate the torque necessary to counter-rotate the tubes at their base, to achieve a prescribed, roughly constant force at the tip 402 of the robot, and the characteristics of the spring mechanism at the base can be tailored accordingly.

Figure 5:
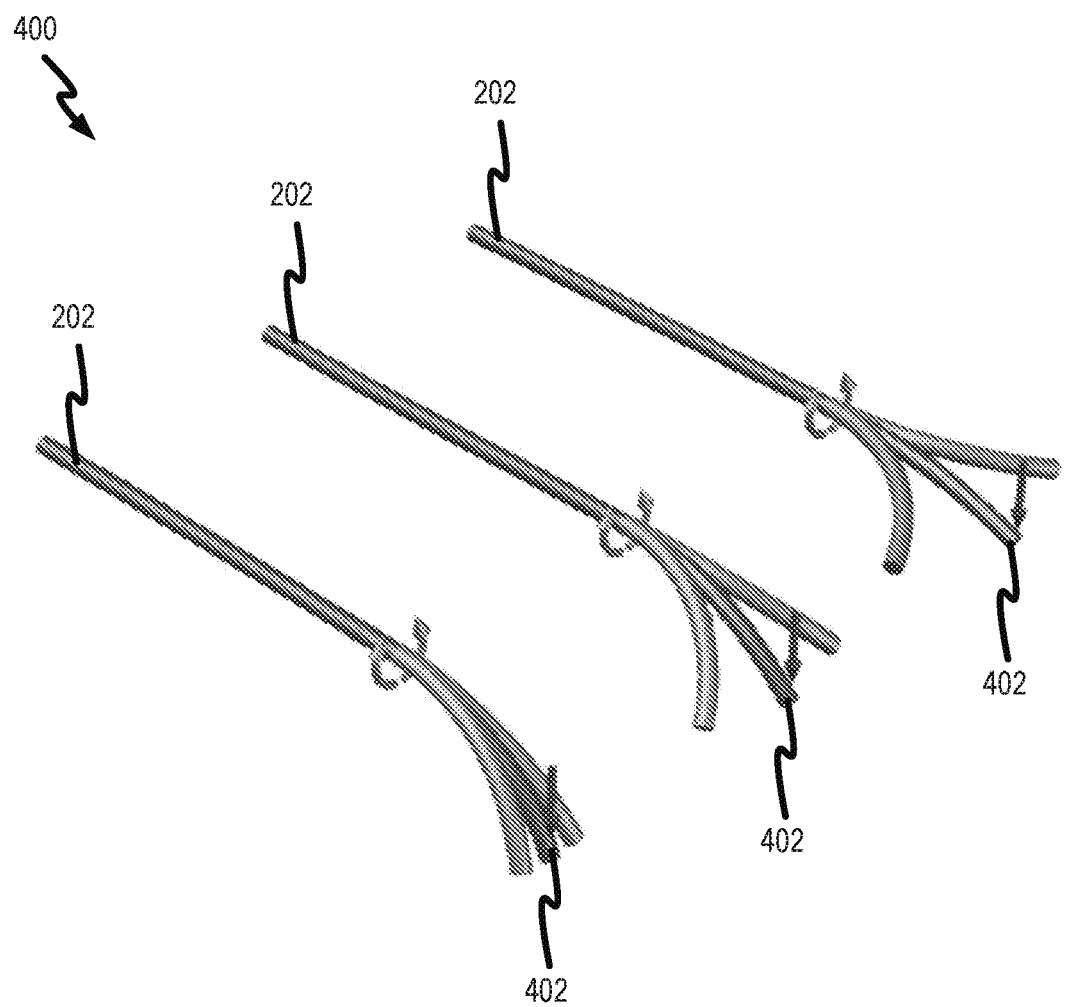
FIG. 5 is a free body diagram illustrating the bi-stable concentric tube robot employing two bi-stable concentric tubes of FIG. 4, in accordance with various embodiments.

FIG. 5 is a free body diagram illustrating the bi-stable tube robot 400 employing two tubes 202, in accordance with various embodiments. A mathematical model can be used to model a constant-curvature distal portion of the bi-stable tube robot 400. The catheter includes two tubes 202, however, the mathematical model can be generalized to account for more tubes. However, it should be noted that regardless of the number of tubes, only the two outer tubes are counter-rotated. In various embodiments, the catheter includes a tube system with three tubes. For example, the three tubes may include two outer, counter-rotating tubes and a central tube. In the concentric arrangement, the central tube can be positioned inside the two tubes and in the eccentric arrangement, the central tube can be positioned between the tubes. The central tube can have a bending stiffness and initial curvature that is different than the bending stiffness and initial curvature of the outer tubes, however, the stiffness and initial curvature may be the same for all three tubes. In various embodiments, the central tube can conform to the mutual curvature of the outer tubes. For example, if the two outer tubes are initially curved and the central tube is initially straight and less stiff compared to the outer tubes, it should bend to attain the curvature of the outer tubes.

Figure 6:
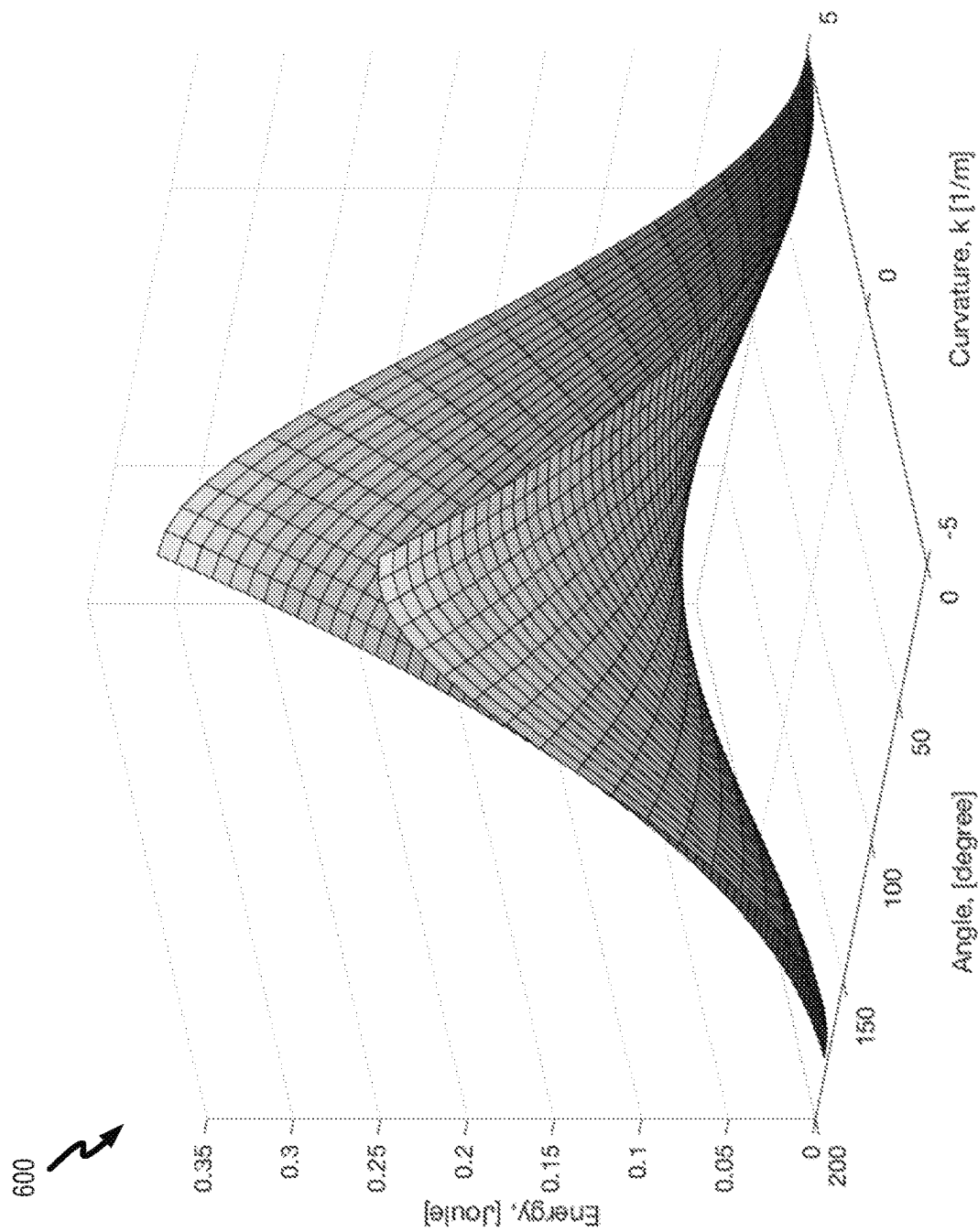
FIG. 6 is an example surface plot of the bi-stable concentric tubes of FIG. 2, in accordance with various embodiments.

In various embodiments, the bi-stable tube robot 400 can include two pre-curved tubes (e.g., tubes 202) that can have the same or similar bending and torsional stiffness or length. The tubes 202 can be counter-rotated at their base (e.g., having the same or similar angle but rotating in two opposing directions). The curvature of the tubes 202 can vary between fully curved up and fully curved down. The maximum curvatures can be the same or similar to the initial pre-curvatures of the tubes 202 and can be referred to as a Balanced Stiffness Tube Pair (e.g., the counter-rotation and the curvature change of the eccentric/concentric tubes can be coupled). When the tubes 202 are fully curved down (e.g., when the counter-rotation is zero, $\theta=0°$) of when $k=k^*=k_{max}$. From being fully curved down, the tubes 202 can be counter-rotated to 90° which corresponds to the straight position where (k=0). As the counter-rotation angle increases to 180, the tubes 202 can reach the second maximum curvature configuration but in opposite directions ($k=-k^*$). FIG. 6 shows an example surface plot 600 with a local minima at ($k=k^*$, $\theta=0°$, Energy=$3.19\times10^{-5}$) and ($k=k^*$, $\theta=180°$, Energy=$2.9\times10^{-4}$). At (k=0, $\theta=90°$, Energy=0.08 J) the point represents a local maxima. Local minimas in the energy plot correspond to stable equilibrium position, while saddle points (local maximas) correspond to unstable equilibrium position. This means that when the tubes 202 are held at 90°, or the straight configuration, any disturbance to the system will cause the tubes 202 to move to either configurations of the maximum curvatures. When a torque is applied to the tubes 202, they can be held in the straight position. When that torque is removed, the tubes 202 can return to either the downward or the upward curvature. The movement of the tubes 202 can be caused by the stored strain energy in the tubes 202 at the straight configuration, which is released when the tubes 202 snap to the remaining two equilibrium configurations.

A. Case of Torsionally-Rigid Tubes

According to various embodiments, a catheter design that includes three-tubes (e.g., tubes 202) can maintain a pseudo-constant contact force at the tip (e.g., tip 402) of the catheter that interacts with the moving cardiac tissue. The potential energy of the three-tubes system can vary upon counter-rotation of the two outer tubes, and the overall curvature. Assuming that the two side tubes have the same pre-curvature $k^*$ and the central tube has an initial curvature $k_c^*$, the potential energy of the system can be a function of the two main kinematic parameters: k and $\theta$, and can be equivalent to the summation of the potential energies of the three tubes.

$$U(\theta, k) = U_L(\theta, k) + U_R(\theta, k) + U_C(\theta, k) \quad (1)$$

$$U(k, \theta) = \frac{1}{2}EI_R L(k - k^*\cos(\theta))^2 + \frac{1}{2}EI_R L(0 - k^*\sin(\theta))^2 + \quad (2)$$
$$\frac{1}{2}EI_L L(k - k^*\cos(\theta))^2 + \frac{1}{2}EI_L L(0 - (-k^*\sin(\theta)))^2 + \frac{1}{2}EI_c L(k - k_c^*)^2$$

where k is the mutual curvature of the tubes and L is the length of the tubes.

Assuming symmetry; that the two side tubes have the same bending stiffness; the equation above can be simplified to;

$$U(k, \theta) = EIL(k - k^*\cos(\theta))^2 + EIL(k^*\sin(\theta))^2 + \frac{1}{2}EI_c L(k - k_c^*)^2 \quad (3)$$

The virtual work theorem can be used, assuming that the work done on the catheter system results from the lateral contact with the tissue and the external torque applied at the base. It can be assumed that the contact force between the tissue and the tip can be always lateral to the tip along the positive y axis.

$$W = F + d\,y + 2Td\theta \quad (4)$$

where y can be the position of the tip along the y axis and equivalent to:

$$y = -(R - R\cos(a)) \quad (5)$$

$$y = \frac{1}{k}(\cos(Lk) - 1) \quad (6)$$

The change in potential energy with respect to the changing counter-rotation angle and the curvature is:

$$dU = \frac{\partial U}{\partial k}dk + \frac{\partial U}{\partial \theta}d\theta \quad (7)$$

Equating Equations (4) and (7) Yields:

$$Fdy + 2Td\theta = \frac{\partial U}{\partial k}dk + \frac{\partial U}{\partial \theta}d\theta \qquad (8)$$

Note that equation (8) can be separable, yielding a system of two algebraic nonlinear equations for the torsion-less eccentric tubes robot represented by (9) and (11):

$$\frac{\partial U}{\partial k} = F\frac{dy}{dk} \qquad (9)$$

where $$\frac{dy}{dk}$$

is:

$$\frac{dy}{dk} = \frac{-1}{k^2}(\cos(Lk) - 1) - \frac{L}{k}\sin(Lk) \qquad (10)$$

$$\frac{\partial U}{\partial \theta} = 2T \qquad (11)$$

By deriving equation (6) and solving for F and T respectively; equations (9) and (11) can be written as:

$$F = \frac{EIL(k - k^*\cos\theta) + \frac{1}{2}EI_CL(k - k_c^*)}{\frac{-1}{k^2}(\cos(Lk) - 1) - \frac{L}{k}\sin(Lk)} \qquad (12)$$

$$T = EILkk^*\sin\theta \qquad (13)$$

B. Case of Torsionally Compliant Tubes

Figure 7:
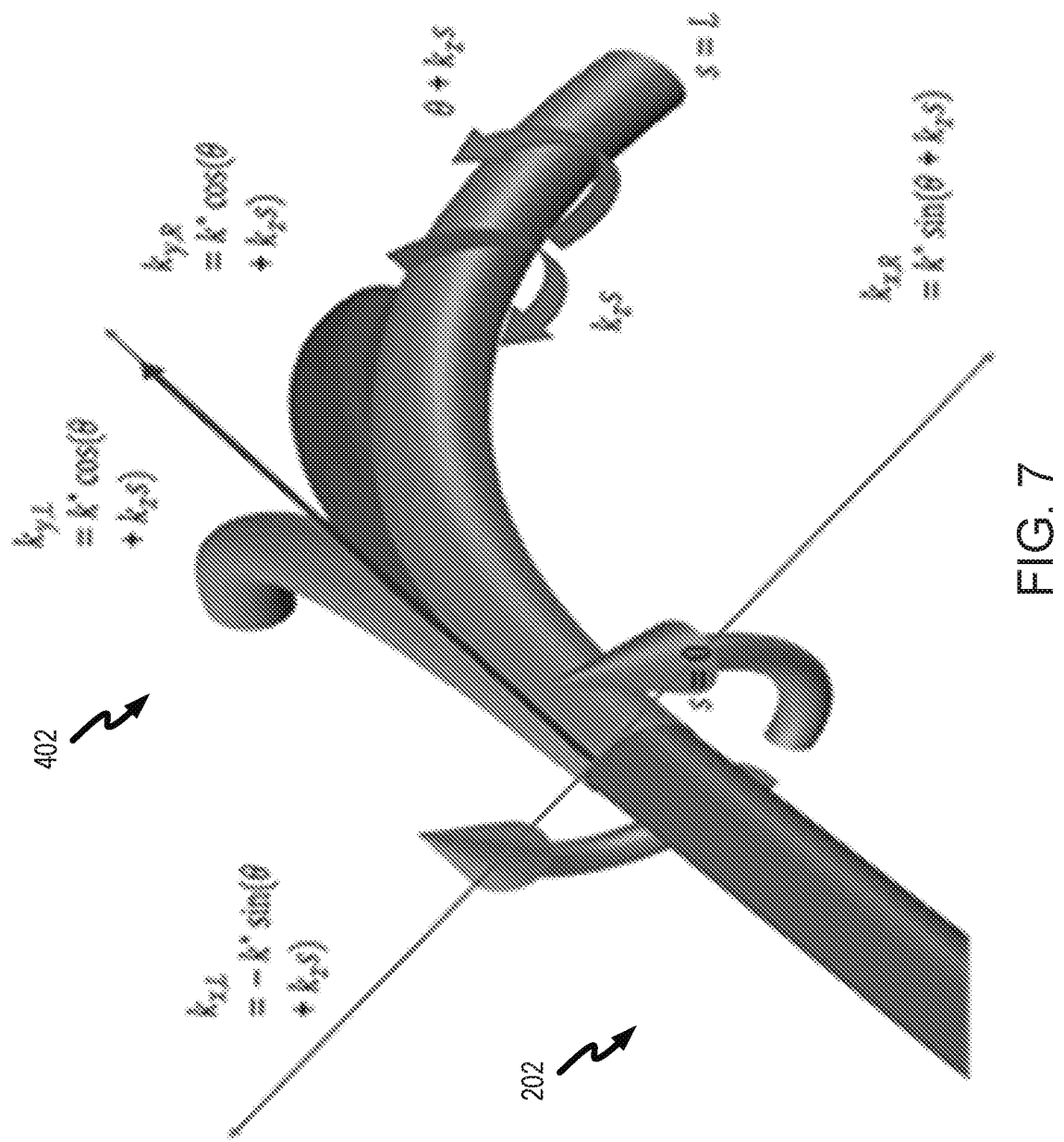
FIG. 7 shows the kinematic parameters of the tubes of the bi-stable concentric tubes of FIG. 2, in accordance with various embodiments.

While infinite torsional rigidity can be assumed, as it was in the previous model, the inevitable phenomenon of twisting due to proximal torques can be applied at the bases of the torsionally-compliant tubes. The potential energy of the system can be a function of the main kinematic parameters: k, the curvature of the tubes, θ, the angle of rotation at the tubes base, and $k_z$, the torsional component equivalent to $$\frac{d\Phi}{ds},$$

where s is the arc-length parameterized position along the curved tubes. FIG. 7 represents the kinematic parameters of the tubes 202, which can be referred to as "Curvature super-position theorem." When the tubes 202 are counter-rotated from 0° to 180°, their curvatures change from k* to −k* due to their bending compliance, and they twist due to their torsional compliance, which results in a change in the total potential energy of the tubes system. The energy of the system is equivalent to the summation of the potential energies of the three tubes as in equation 14. Where R, L, and C denote the right, left, and central tubes respectively.

Potential Energy of the Tubes:

$$U(k, \theta, k_z) = \frac{1}{2}EI_R\int_0^L \left((k - k^*\cos(\theta + k_z s))^2\right)ds + \qquad (14)$$

$$\frac{1}{2}EI_L\int_0^L \left((k - k^*\cos(\theta + k_z s))^2\right)ds +$$

$$\frac{1}{2}EI_R\int_0^L \left((0 - k^*\sin(\theta + k_z s))^2\right)ds +$$

$$\frac{1}{2}EI_L\int_0^L \left((0 - -k^*\cos(\theta + k_z s))^2\right)ds +$$

$$\frac{1}{2}EI_CL(k - k_c^*)^2 + \frac{1}{2}GJ_RL(k_z - k_z^*)^2 +$$

$$\frac{1}{2}GJ_LL(k_z - k_z^*)^2$$

where s can be the arc-length parameterized position along the tubes, $k_z$ can be the torsional component. Assuming symmetry of the two side tubes, equation (14) simplifies to:

$$U(k, \theta, k_z) = EI(\int_0^L \left((k - k^*\cos(\theta + k_z s))^2\right)ds + \qquad (15)$$

$$EI\int_0^L \left((k^*)^2\sin(\theta + k_z s)^2\right)ds +$$

$$\frac{1}{2}EI_CL(k - k^*)^2 + GJL(k_z - (k^*)_z)^2$$

Taking the Partial Derivatives with Respect to k, θ and $k_z$ Respectively Yields:

$$\frac{\partial U}{\partial k} = EI\int_0^L (2k - 2k^*\cos(\theta + k_z s))ds + \qquad (16)$$

$$EI_CL(k - k^*)$$

$$\frac{\partial U}{\partial \theta} = EI\int_0^L (2k^*\sin(\theta + k_z s))(k - k^*\cos(\theta + k_z s))ds + \qquad (17)$$

$$EI\int_0^L 2k^{*2}\sin(\theta + k_z s)\cos(\theta + k_z s)ds$$

$$\frac{\partial U}{\partial k_z} = EI\int_0^L (2k^*s\sin(\theta + k_z s))(k - k^*\cos(\theta + k_z s))ds + \qquad (18)$$

$$EI\int_0^L 2k^{*2}s\sin(\theta + k_z s)\cos(\theta + k_z s)ds +$$

$$2GJL(k_z - k_z^*)$$

Assuming constant torsional deformation (e.g., because there is no external torque/force acting on $k_z$), equation (18) can be set as follows:

$$\frac{\partial U}{\partial k_z} = 0 \qquad (19)$$

Again, Using the Work-Potential Energy Theorem, the Equation can be Solved for F and T:

$$F = \frac{EI\int_0^L (2k - 2k^*\cos(\theta + k_z s))ds + EI_CL(k - k^*)}{\left(\frac{-1}{k^2}(\cos(LK) - 1) - \frac{L}{k}\sin(Lk)\right)} \qquad (20)$$

-continued $$T = \frac{\partial U}{\partial \theta} \quad (21)$$

$$T = EI \int_0^L (2k^* \sin(\theta + k_z s))(k - k^* \cos(\theta + k_z s)) ds + \quad (22)$$

$$EI \int_0^L 2k^{*2} \sin(\theta + k_z s) \cos(\theta + k_z s) ds$$

The simulation process of the mathematical model described in the previous section starts with the characterization of the mechanical and geometrical properties of the tubes (VASCOTUBE, Germany) as shown in table 1. Tubes were pre-curved using rapid NITINOL heating and the process can be described in more detail in the next section. With a priori knowledge of the workspace of the catheter, of the input in the simulation can be always k, resulting in a determined system of equations, in both torsional rigidity and torsional compliance cases. The simulation process can be performed on two stages: the objective of the first stage can be to find the torque required to maintain the prescribed force at the tip at small ranges of k. In the second stage, a function $T(\theta)$ can be interpolated and used to design the passive control mechanism for the proximal torque. MATLAB lsqnonlin may be used to solve some or all of the equations.

TABLE I

CHARACTERISTICS OF THE TUBES USED FOR THE PROTOTYPE

| | |
|---|---|
| Outer Diameter | 1.8 mm |
| Inner Diameter | 1.4 mm |
| Radius of Curvature | 200 mm |
| Angle of Curvature | 45 |
| Tubes Length | 157 mm |
| Bending Stiffness | 0.02058 Nm2 |
| Torsional Stiffness | 0.155 Nm2 |

Numerical Analysis

At the small ranges of the curvature, a constant torque can be applied at the base of the tubes such that the force at the tip falls within the accepted range of contact during ablation (0.1 N to 0.4 N). A point can be selected from every range and recorded, the force value which satisfies the surgical requirement, the corresponding curvature, angle of counter-rotation along with the input torque applied at the base, as shown in tables 2 and 3, representing the obtained values of the torsionally rigid and the torsionally compliant tubes respectively. It should be noted that the purpose of the applied torque can be to compensate the force at the tip, as they are inversely related.

TABLE II

TORSIONALLY-RIGID MODEL

| Curvature(m$^{-1}$) | Applied Torque (Nm) | Force (N) | Angle (degrees) |
|---|---|---|---|
| 4.6 | 0 | 0.243 | 0 |
| 4.15 | 0.025 | 0.295 | 21.6 |
| 3.81 | 0.033 | 0.280 | 30.9 |
| 3.23 | 0.036 | 0.244 | 42.9 |
| 2.82 | 0.035 | 0.244 | 49.3 |
| 2.16 | 0.030 | 0.246 | 58.1 |
| 1.70 | 0.025 | 0.266 | 64.0 |
| 1.31 | 0.020 | 0.263 | 68.9 |
| 0.96 | 0.015 | 0.281 | 72.7 |
| 0.31 | 0.005 | 0.284 | 80.3 |

TABLE III

TORSIONALLY-COMPLIANT MODEL

| Curvature (m$^{-1}$) | Applied Torque (Nm) | Force (N) | Angle (degrees) | kz |
|---|---|---|---|---|
| 4.6 | 0 | 0.243 | 0 | 0 |
| 4.3 | 0.020 | 0.293 | 19.3 | −0.61 |
| 4.0 | 0.030 | 0.258 | 31.5 | −0.92 |
| 3.55 | 0.035 | 0.249 | 42.0 | −1.09 |
| 3.23 | 0.036 | 0.239 | 48.1 | −1.12 |
| 2.8 | 0.035 | 0.232 | 54.8 | −1.10 |
| 2.42 | 0.032 | 0.284 | 58.5 | −1.01 |
| 1.87 | 0.027 | 0.258 | 65.9 | −0.86 |
| 1.31 | 0.02 | 0.260 | 71.8 | −0.64 |
| 0.96 | 0.015 | 0.279 | 74.9 | −0.48 |
| 0.31 | 0.005 | 0.284 | 81.0 | −0.16 |

The relationship between T and $\theta$ can be deduced, which can result in a passively controlled catheter. Stated alternately, by ensuring that the torque applied at the base always results in the desired force, at all curvatures, the passively controlled robotic catheter for cardiac ablation can be achieved. The torque can be fit to values of a function $T(\theta)$, and used to aid in the design of the actuation mechanism described herein. This can be the main step that results in passive control of the tubes rotation for optimal tip force. The table below shows the torque value applied at the tip and the corresponding base angle, curvature and tip force. The interpolated $T(\theta)$ can be selected such that (1) the Error can be minimized and (2) the resultant force can be bounded between 0.1 N and 0.4 N. Exploring positive curvatures (tubes curved down) and/or a more generalized approach can be used.

For the Case of Torsionally Rigid Model, the Interpolated Torque Function can be:

$$T(\theta) = 0.033 \sin(2\theta) + 0.003 \quad (23)$$

while for torsionally complaint model, it is:

$$T(\theta) - 0.033 \sin(2\theta) \quad (24)$$

Tables 4 and 5 also illustrate high proximity between the actual and the interpolated torques, especially in the case of the torsional compliance model with an absolute mean error of only 0.1%, compared to 0.25% in the preliminary model of pure bending. It should be noted that the discussed methodology can also be extrapolated to fit the negative curvatures (tubes are curved upward).

TABLE IV

TORSIONALLY-RIGID MODEL

| Applied Torque (Nm) | Angle (degrees) | Interpolated Torque (Nm) |
|---|---|---|
| 0 | 0 | 0 |
| 0.025 | 21.6 | 0.0226 |
| 0.033 | 30.9 | 0.0291 |
| 0.036 | 42.9 | 0.0329 |
| 0.035 | 49.3 | 0.0326 |
| 0.030 | 58.1 | 0.0296 |
| 0.025 | 64.0 | 0.0260 |
| 0.020 | 68.9 | 0.0221 |
| 0.015 | 72.7 | 0.0187 |
| 0.005 | 80.3 | 0.0110 |

TABLE V

TORSIONALLY-COMPLIANT MODEL

| Actual Torque (Nm) | Angle (degrees) | Interpolated Torque (Nm) |
|---|---|---|
| 0 | 0 | 0 |
| 0.020 | 19.3 | 0.0206 |
| 0.030 | 31.5 | 0.0294 |
| 0.035 | 42.0 | 0.0328 |
| 0.036 | 48.1 | 0.0328 |
| 0.035 | 54.8 | 0.0311 |
| 0.032 | 58.5 | 0.0294 |
| 0.027 | 65.9 | 0.0246 |
| 0.02 | 71.8 | 0.0196 |
| 0.015 | 74.9 | 0.0166 |
| 0.005 | 81.0 | 0.0102 |

1. EXPERIMENTAL VALIDATION

A. Shape Setting of NITINOL Tubes

Figure 8:
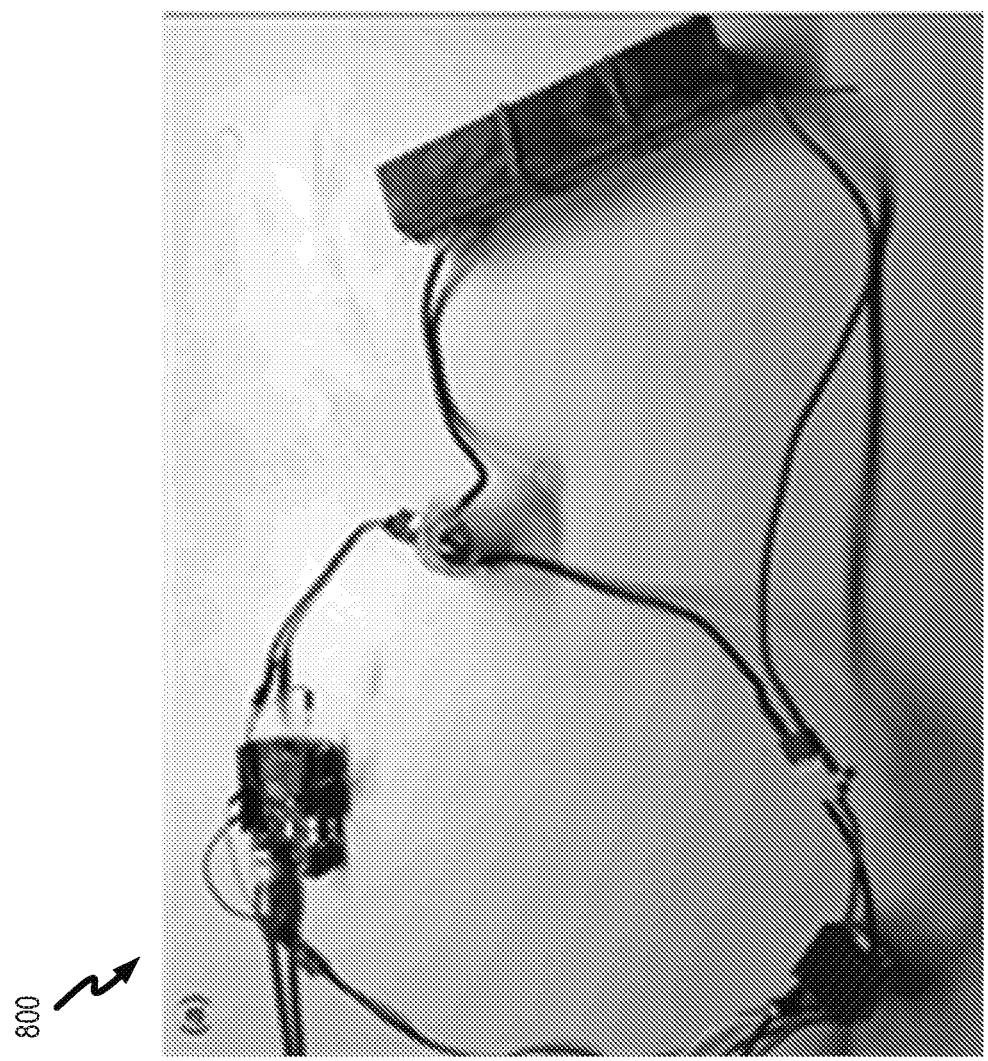
FIG. 8 shows a system for shaping tubes for use with the bi-stable concentric tubes of FIG. 2, in accordance with various embodiments.

FIG. 8 shows a system 800 for shape setting tubes 202 for use with the robotic catheter 200, in accordance with various embodiments. The NITINOL tubes can pre-curved using rapid electrical heating, with real time measurements of the current through and the voltage across each tube. Using tube resistance feedback control, the tubes can be heated up to 500° Celsius, thereby ensuring that they retain the desired curvature and maintain their superelasticity. An Arduino microcontroller code of real time voltage and current control may be written using the relationship between the resistance and the temperature of NITINOL tubes. An Electronic Speed Controller (ESC), along with a LiPo battery of 7.4 V, can be used to control the Pulse Width Modulation (PWM) signal delivered to the ESC by the Arduino microcontroller. A Hall Effect-based current sensor may be used to obtain real-time measurements of the current running through the tube. The Hall Effect-based current sensor may include a magnetic field sensor (KY 036) placed around a coil. The sensor may be calibrated using a conventional power supply, thereby exploiting the high linearity between magnetic field and electric current. To halt the effect of fast switching, a low pass filter may be used to smooth the measurements, using a 100 microF capacitor and a 3.3 k ohms resistor. Regarding the fixture, a CNC machine may be used to create a slot in laminated wood.

B. Eccentric Tubes Setup

Figure 9:
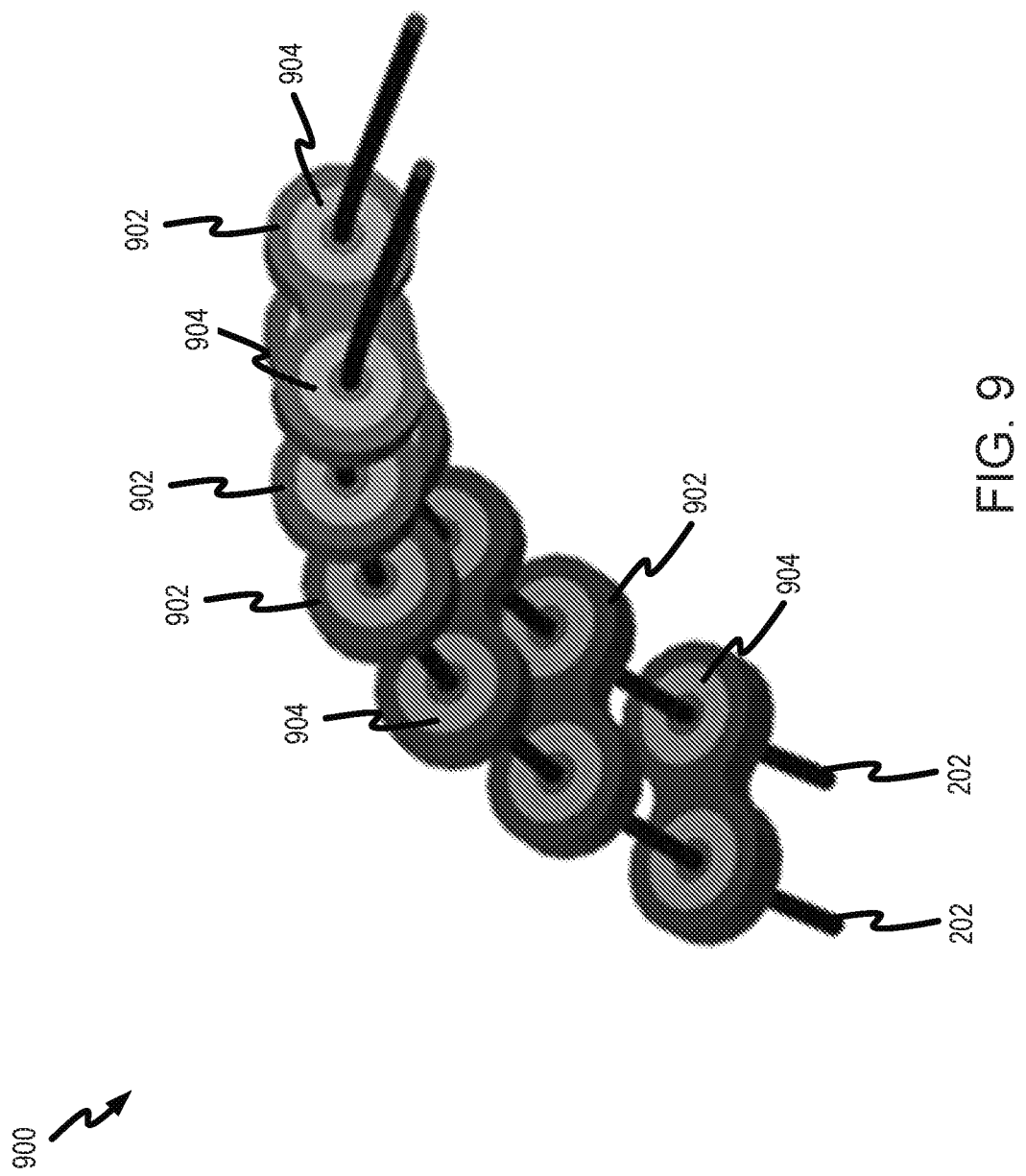
FIG. 9 shows an arrangement of eccentric tubes for use with the connected to one another by vertebrae and held in position by bearings, according to various embodiments.

FIG. 9 shows an eccentric tube assembly 900 including tubes 202 connected to one another via vertebrae 902 and held in place by bearings 904, according to various embodiments. The two main design criteria of the proposed concentric tube catheter are that the two outer tubes possess the same bending and torsional stiffnesses, and that friction between the tubes is minimized. The eccentric tube assembly 900 may be used to test the concentric tube design. The eccentric tube assembly 900 can use bearings 904 that separate a vertebra 902 from the tube 202, thereby eliminating the impact of friction as well as contact forces with the tubes wall. The bearings 904 may be or include 4 mm thick, stainless steel shielded bearings (SKF) with an outer diameter of 9 mm and an inner diameter of 4 mm. The vertebrae 902 may be spaced (e.g., equally spaced) to form a robotic backbone of two tubes 202 separated by an offset distance of 13.3 mm. The vertebrae may be formed via additive manufacturing or other suitable method, including 3D printing using Acrylonitrile Butadiene Styrene (ABS).

C. Compliant Mechanism Design

Figure 10:
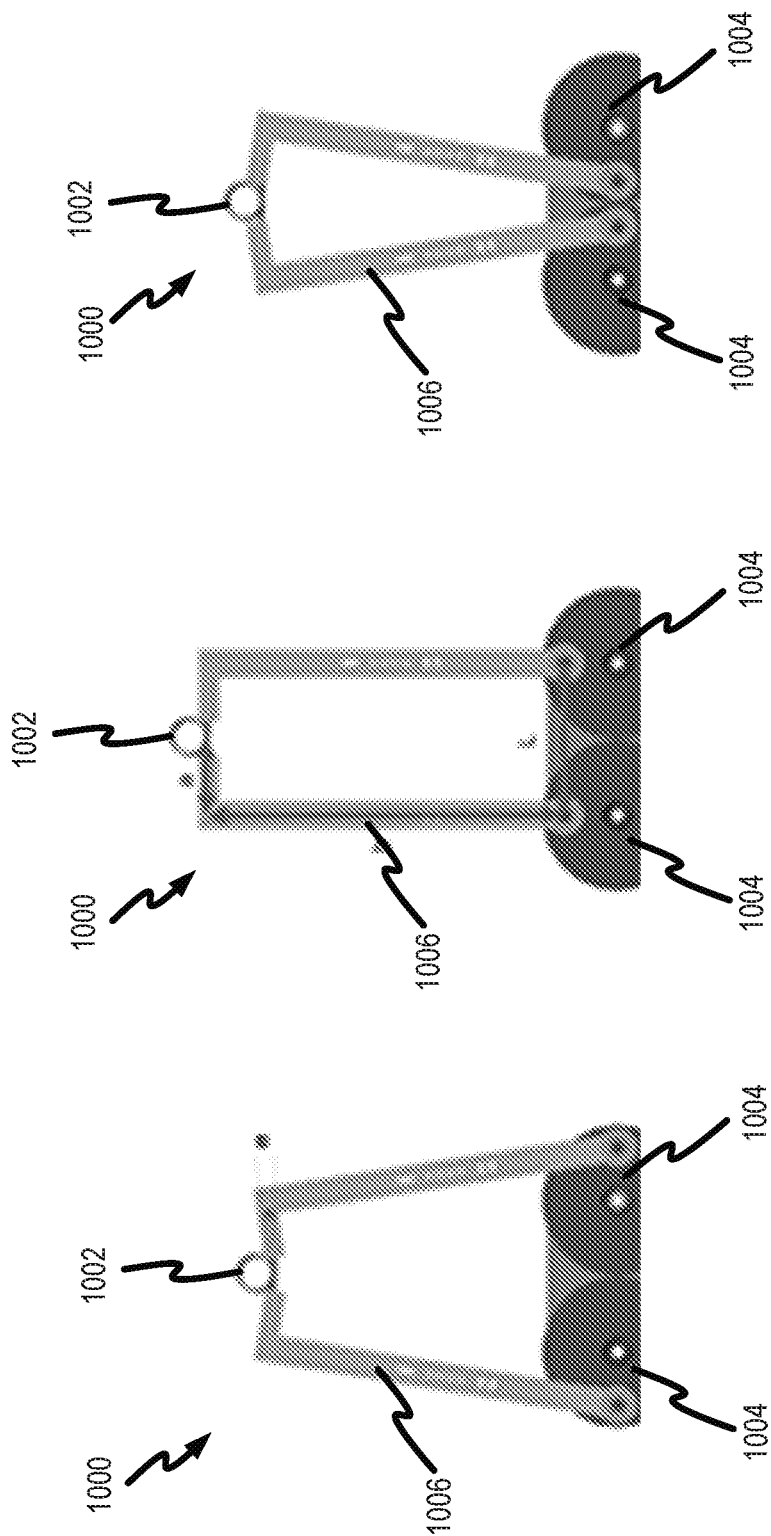
FIGS. 10A, 10B, and 10C are schematic illustrations of a compliant mechanism for use with the eccentric tubes of FIG. 9, the compliant mechanism including a spring connected to gears for rotating the eccentric tubes, according to various embodiments.

FIGS. 10A through 10C are schematic illustrations of a compliant mechanism 1000 and FIGS. 11A through 11C are another view of the compliant mechanism for use with the eccentric tubes of FIG. 10, the compliant mechanism including a spring 1002 connected to gears 1004 for rotating the eccentric tubes 202, according to various embodiments. The compliant mechanism 1000 may be an example of spring mechanism 204. The spring 1002 can be positioned a distance away from the gears 1004 and connected to the gears via links 1006. The gears 1004 can counter-rotate and can cause movement of the links 1006, which in turn causes torque around the center of the spring 1002. The torque around the center of the torsional spring can result in a deflection angle (alpha). Geometrically, a q relationship between this angle and the horizontal length (L) can be established. The implicit function can be solved numerically for T using the equation below.

$$L = 2a \cos(T/k) + 2b \sin(T/k) \tag{25}$$

The Force Acting at the Gear Edges can be Calculated Using:

$$F = \frac{T}{a\sin\left(\frac{T}{k}\right) - b\cos\left(\frac{T}{k}\right) - 0.005} \tag{26}$$

Hence, the torque acting on the tube base can be found by multiplying the obtained force by the moment arm:

$$\text{Torque} = 0.015 F \cos \Theta \tag{27}$$

where $\Theta$ can be the angle of gear rotation.

Figure 12:
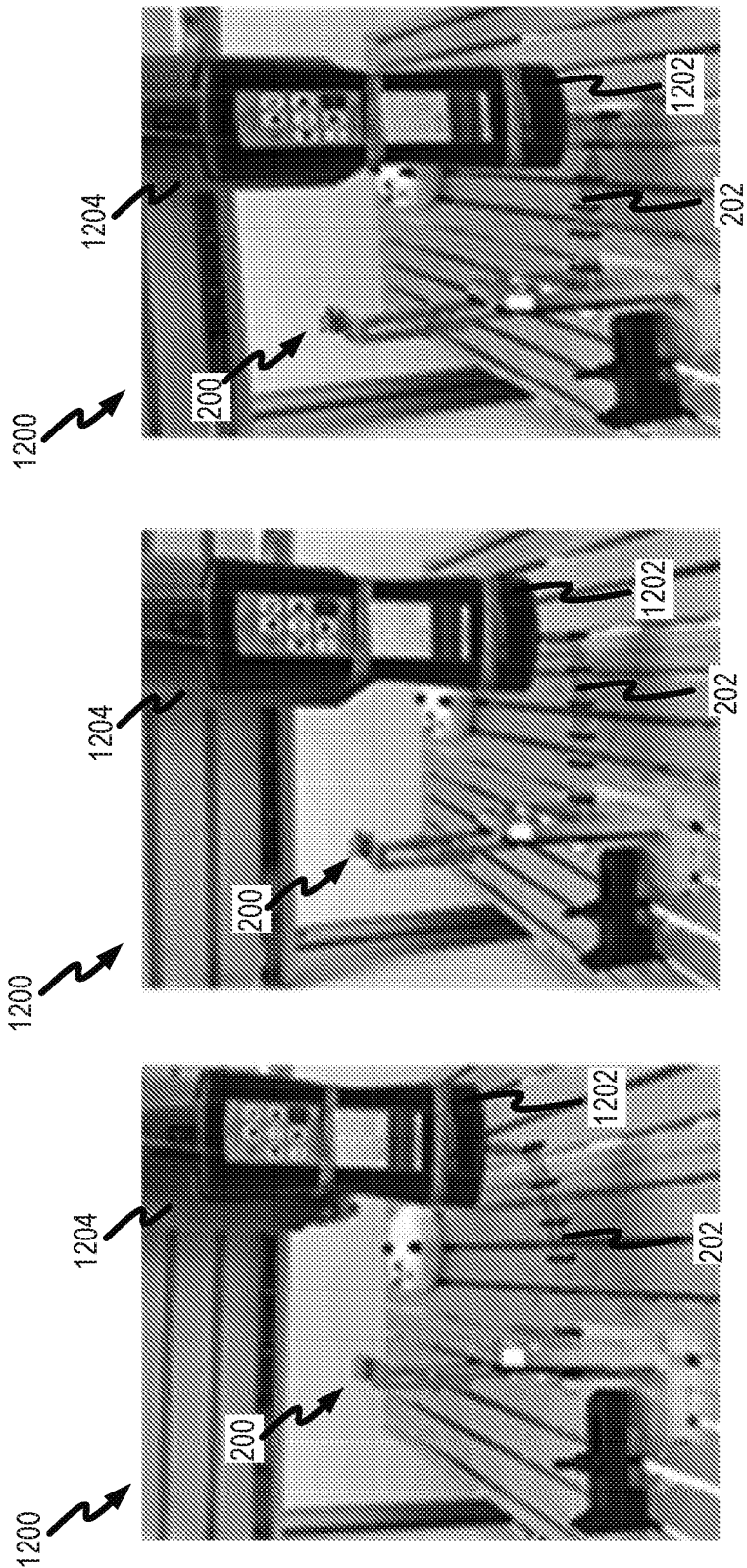
FIGS. 12A, 12B, and 12C show an example of an experimental setup of the compliant mechanism and eccentric tubes of FIGS. 11A, 11B, and 1C, according to various embodiments.

An example of a robotic catheter 200 positioned in a testing apparatus 1200 is shown in FIGS. 12A through 12C, according to various embodiments. The testing apparatus 1200 includes a PCE 802 force sensor connected to a CNC machine 1204. During testing the −z axis displacement is incremented by 5 mm downward starting from 0 mm to 45 mm. (e.g., to simulate the tip moving in response to contact with the moving heart tissue). Importantly, the vertical length b was set to 77 mm, while the fixed a distance can be always equivalent to the radius of the gear, which can be 21.45 mm.

Figure 13:
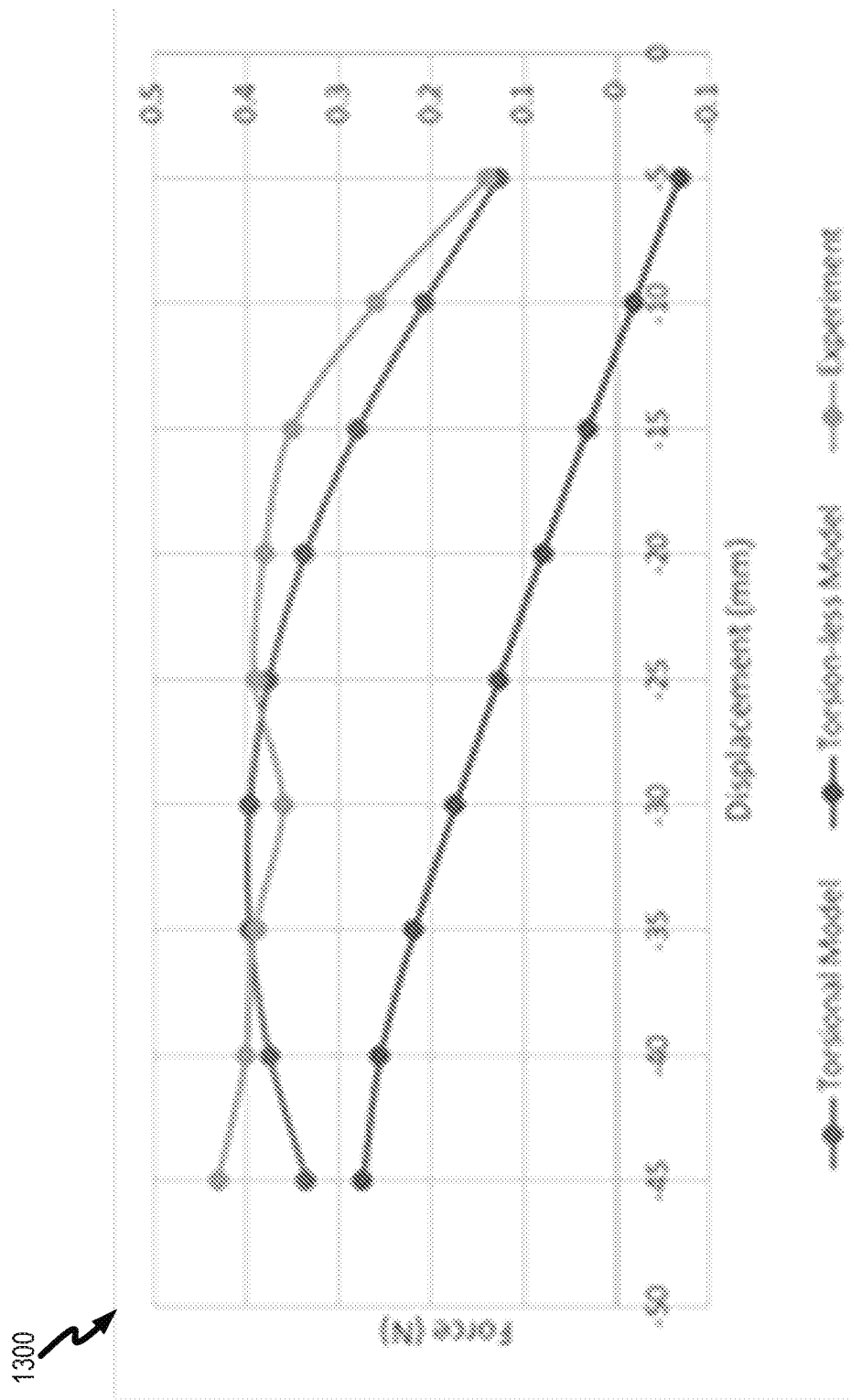
FIG. 13 is a graphical representation showing experimental and numerical results of the displacement of the eccentric tubes of FIGS. 12A, 12B, and 12C, with force on the y-axis and displacement on the x-axis, according to various embodiments.
Figure 14:
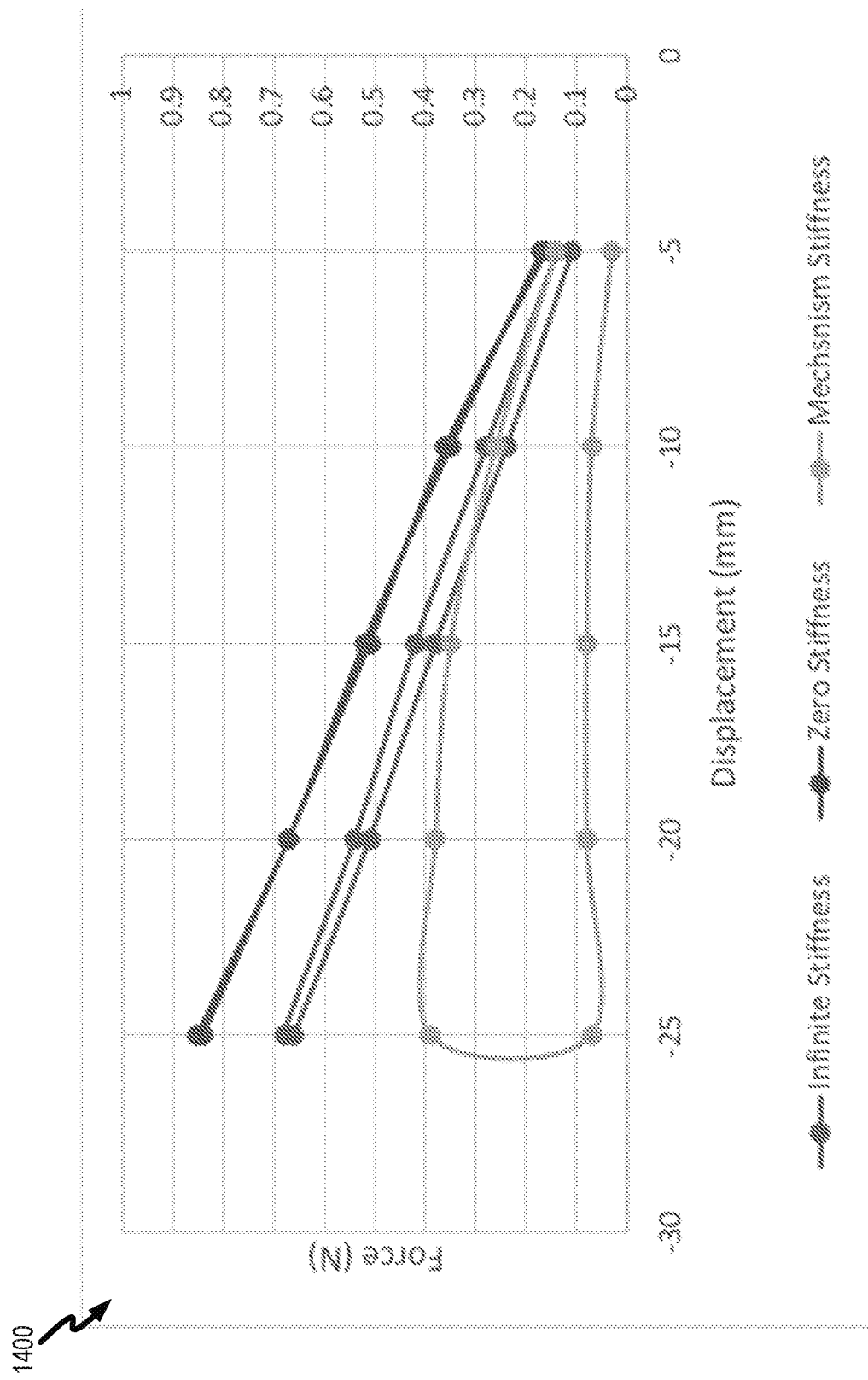
FIG. 14 is a graphical representation of the displacement of the eccentric tubes of FIGS. 12A, 12B, and 12C based on various stiffnesses of a torsional spring, with force on the y-axis and displacement on the x-axis, according to various embodiments.
Figure 15:
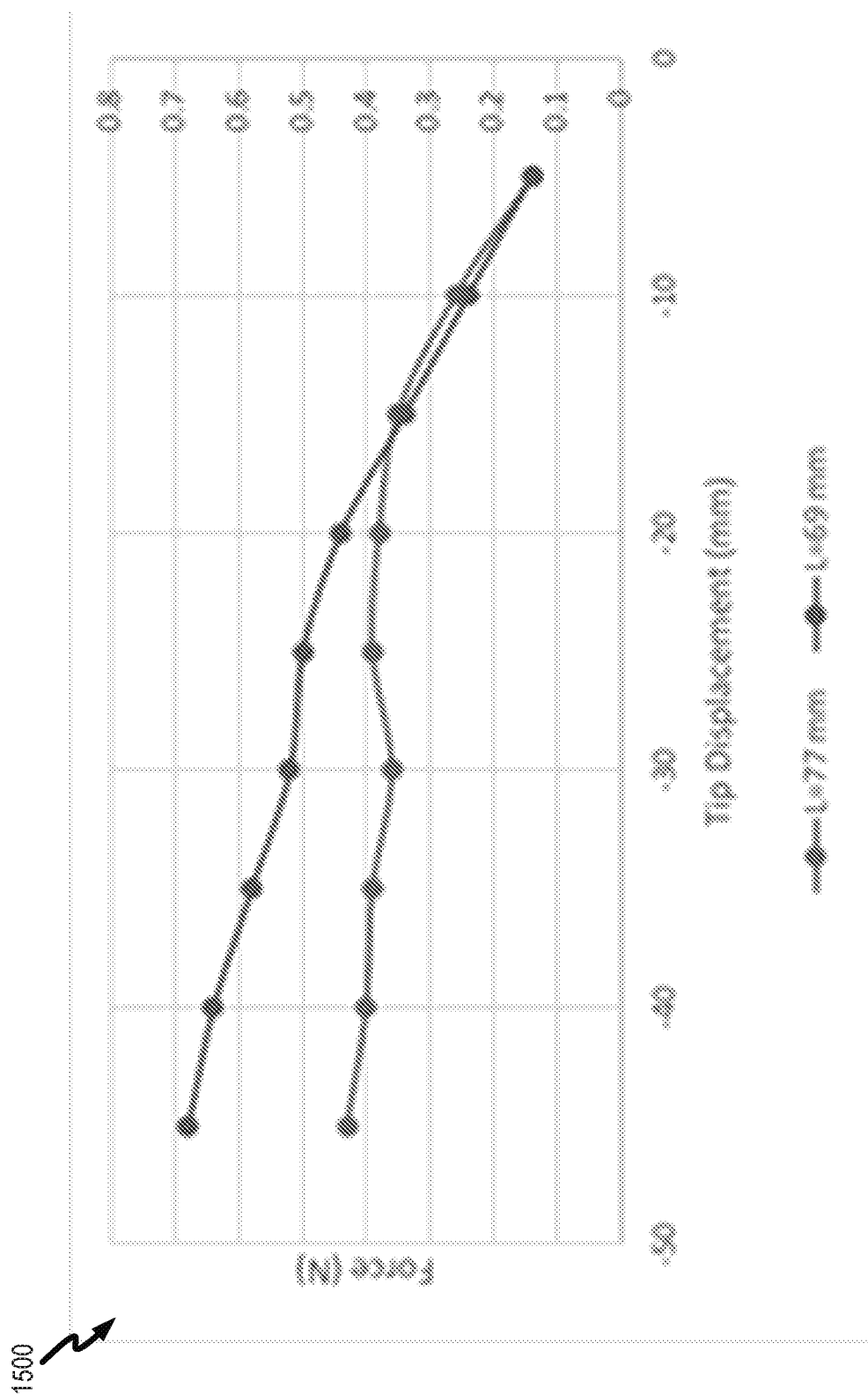
FIG. 15 is a graphical representation of the displacement of the eccentric tubes of FIGS. 12A, 12B, and 12C showing the effects of varying the distance between the spring and the gears connected to the eccentric tubes, with force on the y-axis and displacement on the x-axis, according to various embodiments.
Figure 16:
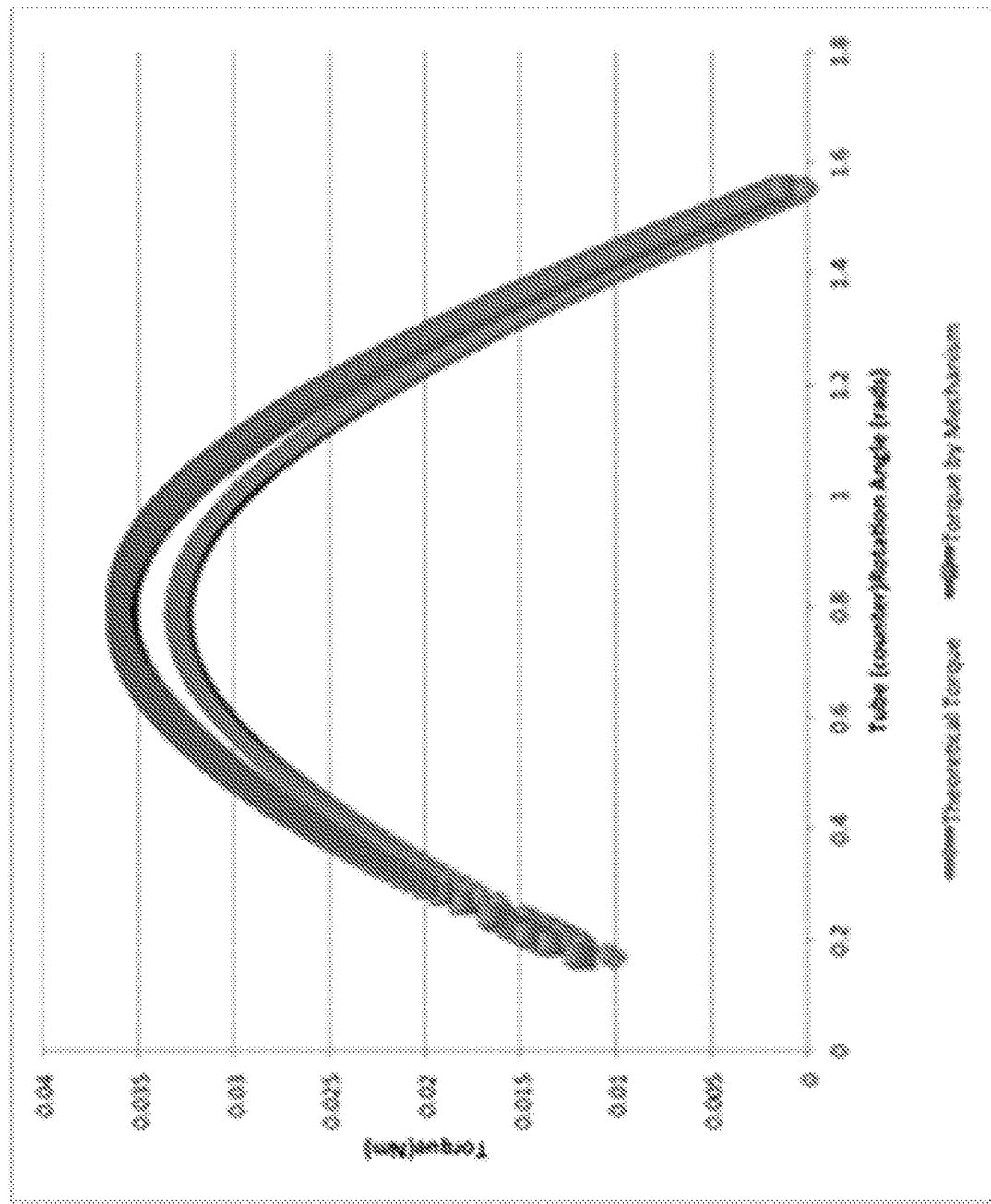
FIG. 16 is a graphical representation of the theoretical and actual torque and the rotation angle of the eccentric tubes of FIGS. 12A, 12B, and 12C, according to various embodiments.
Figure 17:
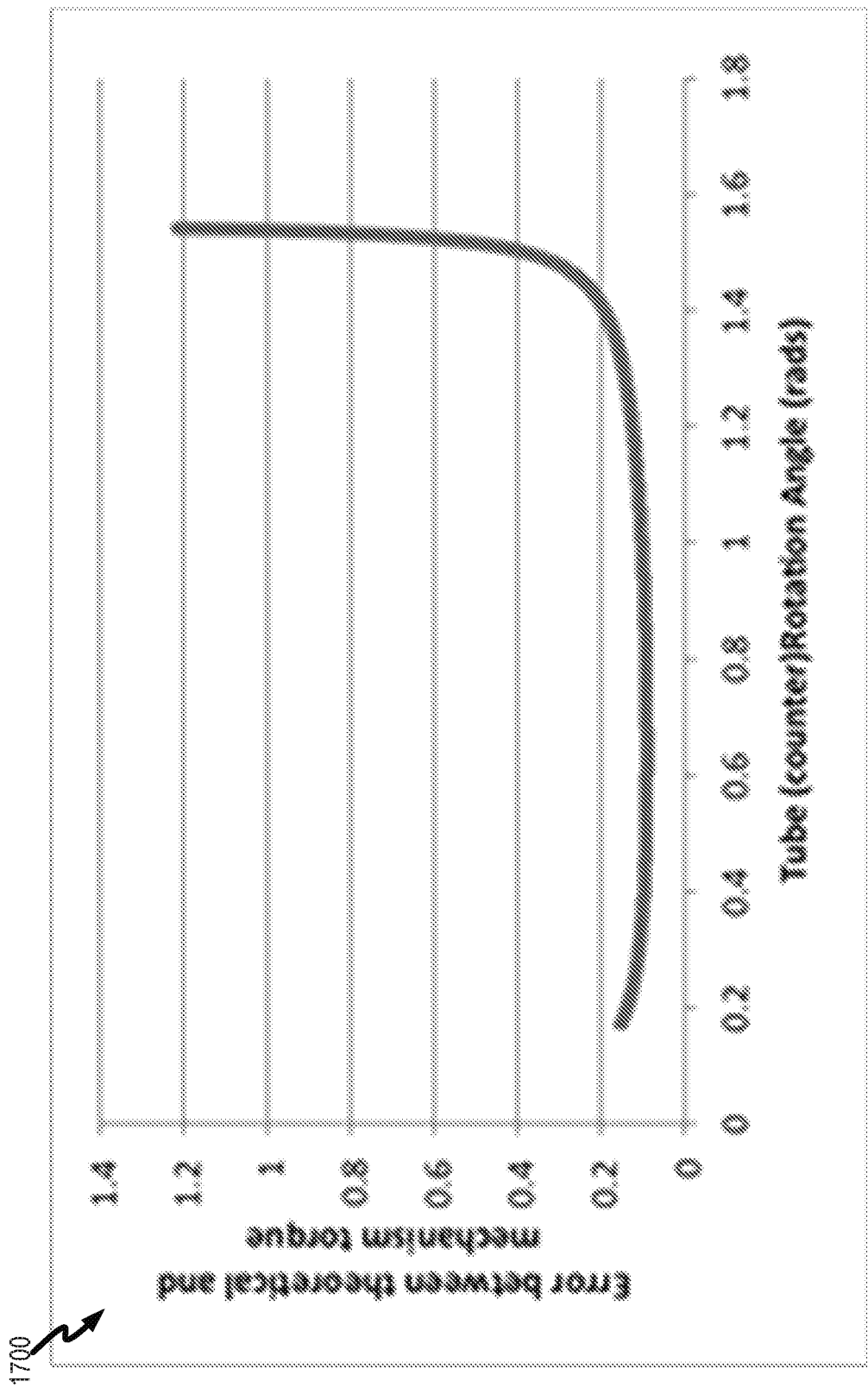
FIG. 17 is a graphical representation of the error between the theoretical and actual torque of FIG. 16, according to various embodiments.

FIGS. 13 through 15 are graphical represents showing data collected using the robotic catheter 200 using the testing apparatus 1200 of FIGS. 12A through 12C and numerical results obtained using the equations discussed herein. To prove the success of the proposed passive stiffness control mechanism at the base of the robotic catheter, the prototype was tested under two other cases, namely case A and case B. For, case A, the spring mechanism was completely removed from the robot's base, and the tubes were allowed to freely rotate, while in case B, the tubes were pre-stressed to the straight singularity position, before a force was applied at the tip all the way downward. Cases A and B were compared with case C, which was designed with the spring mechanism attached to the eccentric tubes. FIG. 13 shows a graphical representation 1300 that shows how the proposed mechanism successfully flattens the curve of the force displacement.

Specifically, FIG. 14 is a graphical representation 1400 showing experimental and numerical results of the displacement of the eccentric tubes 202 of FIGS. 12A through 12C, with the tip force on the y-axis and the tip displacement on the x-axis. FIG. 15 is a graphical representation 1500 of the displacement of the eccentric tubes 202 of FIGS. 12A through 12C showing the effects of varying the length of the links 210 (i.e., the distance between the spring 206 and the gears 108), with force on the y-axis and displacement on the x-axis, according to various embodiments.

Figure 11:
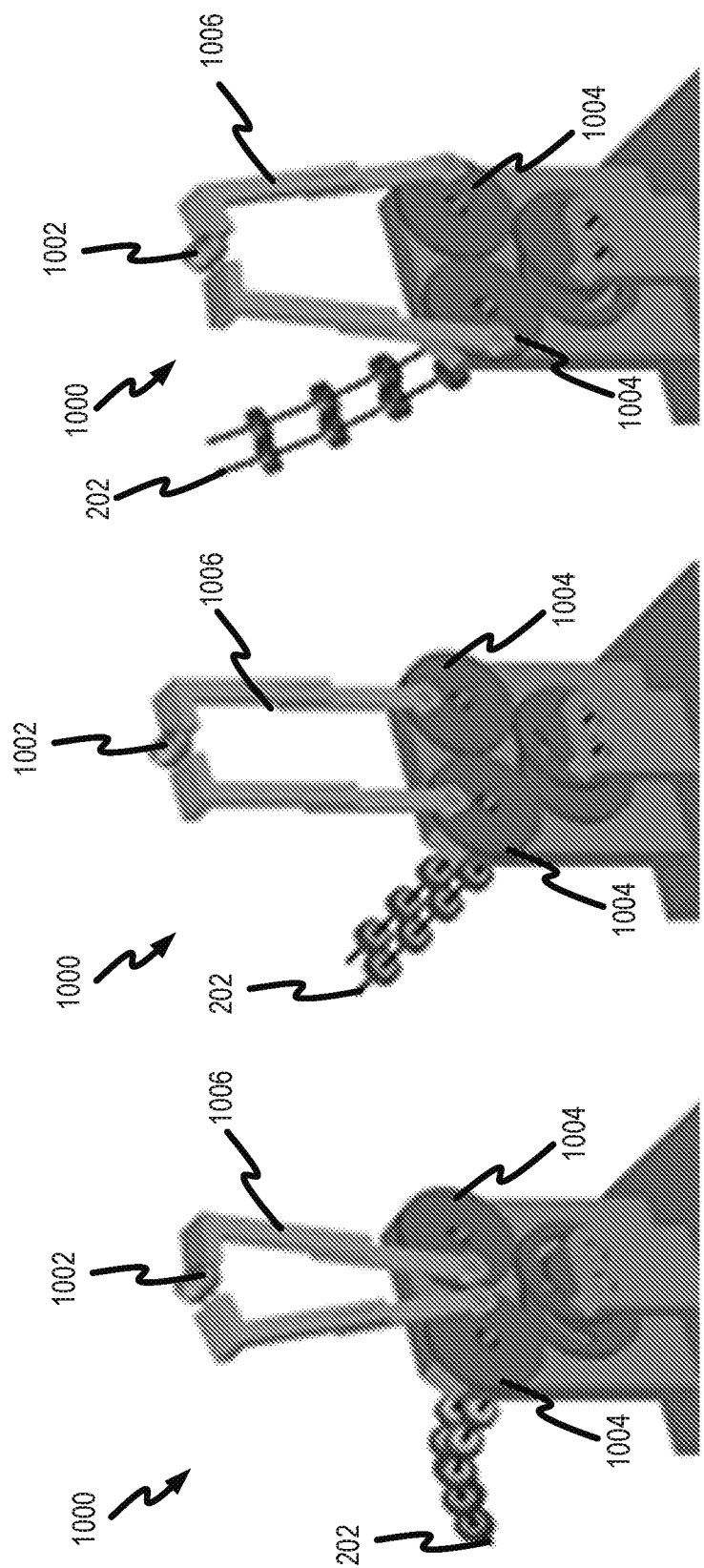
FIGS. 11A, 11B, and 11C show an example compliant mechanism and eccentric tubes for use with the eccentric tubes and compliant mechanism of FIGS. 9, 10A, 10B, and 10C, according to various embodiments.

The impact of the length of the links connecting the spring to the upper gears showed that reducing this length increases the tip force as illustrated in FIG. 11. In various embodiments, the optimal length, as per the selected prototype design parameters, can be 77 mm, which can be 9.4% different from the theoretical value, obtained from mechanism simulation results, which was 85 mm.

FIGS. 13 through 17 can be used to determine the absolute error in tip force when the values generated by the model are compared with the valued obtained using the testing apparatus 1200 with the robotic catheter 200. Comparing the measured and model generated values, it can be determined the experimentally measured tip forces are closer to those of the torsionally compliant model, reflecting the significance of torsional deformation when a proximal torque can be exerted on the tubes 202 for counter-rotation. The torque of the robotic catheter 200 at various angles is shown in graph 1600 of FIG. 16. The mean absolute error in tip force can be 3.94% in the case of torsional model and 22.5% can be the case of torsion-less model. The percentage error between the actual torque required for the counter-rotation of the tubes which can be obtained from the concentric tubes model and the torque obtained from simulating the mechanics of the spring and gears system is shown in graph 1700 of FIG. 17. Based on the torsionally compliant models disclosed above, the error is within a suitable range and the robotic catheter 200 is therefore suitable for use in minimally invasive cardia surgeries.

In addition, from FIG. 13 showing the graphical representation 1300 of the displacement of the eccentric tubes 202, it can be deduced that the proximal, (variable)-stiffness mechanism for distal force control can be associated with hysteresis, as opposed to the rest trials of zero and infinite stiffness. In fact, hysteresis can be a non-negligible phenomenon in compliant robotic joints with nonlinear stiffness. Besides the variable stiffness, the phenomenon also arises from internal friction between the torsional spring coils and the gears teeth. In fact, the idea that there are two levels of pseudo-constant tip force due to hysteresis, can also be somehow exploited and can have high potential impact for future improvement. Considering the viscoelasticity nature of the heart tissue, and its variable mechanical properties through the cardiac cycle, a lower constant force can be sufficient when the heart is contracting as it becomes stiffer, while a higher constant force is required when the heart is relaxing, as it becomes softer.

The behavior of the catheter prototype can be very sensitive to the length b, which in fact has the highest impact of the distal behavior of the tip, the design of multiple slots not only permits reusability and repeatability, but also withstands the use of tubes with other mechanical and geometrical dimensions, for which the length can be changed to obtain prescribed tip forces. Furthermore, an initial condition of spring pre-stretching or pre-compressing can be viable. The idea of preload can be important to achieve an initial, specific torque other that zero, if required.

Although the catheter was tested with eccentrically arranged tubes, the aforementioned mechanisms and models are also applicable to a robotic catheter utilizing concentric tubes. In this regard, two (or more) NITINOL concentric tubes with different diameters and the same bending and torsional stiffnesses can be used. The common bending and torsional stiffnesses are achievable by modifying the bending and torsional stiffness of one or both tubes by creating grooves on the tube wall, by thickness selection, or other structural modifications.

Alternatively, eccentric arrangements of the tubes can be also used for cardiac catheters, whereby the tubes and vertebrae can be rescaled based on the actual range of motion of the heart tissue (usually 1-2 mm) and placed in an external sheath, resulting in a miniaturized eccentric tube catheter.

Another example of a robotic catheter 1800 positioned in a testing apparatus 1802 is shown in FIG. 18, according to various embodiments. The robotic catheter 1800 can include a phantom silicon tissue. A proximal spring can be attached to the base of the robotic catheter 1800. the proximal mechanism can cause a constant tip force and compensated deformation between the robot curvature and the moving heart tissue. Removing the proximal mechanism can result in larger deformation of the phantom tissue. For example, while the robot curvature is not changing due to the absence of the optimal proximal torque. The tissue deformation can be dangerous if occurred during electrophysiology interventions because it may lead to heart perforation. The proximal mechanism can aid in maintaining optimal contact but also procedural surgery. For example, by keeping the tip force within the desired range regardless of the tissue displacement.

In various embodiments, a higher level of force can occur when a curvature of the robotic catheter 1800 changes from straight to a downward curvature, which can interject energy on the moving wall of a heart. However, when the curvature changes from fully curved down to the straight configuration, the level of the force gets lower but may remain constant against the heart wall.

Efficiency is a measure of energy losses within a system. Energy losses can take place in the system due to the gears in a proximal compliant mechanism. Rolling bearings can be placed between the tubes and the vertebrae, which can reduce or eliminate frictional forces along the robotic backbone. When there is torque transmission between the gears, the frictional forces between their teeth can result in load-dependent energy dissipation. The input torque in the system can result from a downward force acting on the tip, and is manifested by the torque facilitating the counter-rotation of the tubes at their base. The torque can then be transmitted from the tubes to the spring. The frictional forces can reduce the torque transmitted from the tubes to the spring.

Passively controlled catheters as described herein can be controlled manually without the need for computerized real-time monitoring or sensors, and thus can be of high clinical impact. The design-based control system naturally results in consistent contact with the tissue of interest, even when the tissue is moving, and may preclude the need for repetitive manual manipulation of the catheter that could otherwise cause injury. Such system can also reduce the surgical time, by eliminating the need for computationally inefficient control architectures that depend on predictive filters of heart motion. By eliminating the need for sensors, the robotic catheter can be MRI-compatible, and/or even more miniaturized by no longer needing to incorporate sensors and the associated components (e.g., wires). Most importantly, the robotic catheters described herein can achieve increased intraoperative force control by leveraging concentric tube robots having inherently high mechanical robustness.

What can be claimed is:

1. A robotic catheter, comprising:
   a concentric arrangement of a first tube and a second tube arranged concentrically around the first tube, the first tube having a first bending resistance and a first torsional resistance, and the second tube having a second bending resistance and a second torsional resistance, wherein the first and second tubes are moveable between a first position and a second position, and wherein in the first position a first end of the first and second tubes apply a first force to a tissue and in the second position the first and second tubes apply a second force to the tissue; and
   a torsional spring positioned at a second end of the concentric arrangement of the first and second tubes and coupled with the second end of the concentric arrangement of the first and second tubes, such that, when the first tube and the second tube move between the first position and the second position, the torsional spring causes the first and second tubes to counter-rotate relative to one another, causing the first end of the first and second tubes to transition between applying the first force and the second force.

2. The robotic catheter of claim 1, wherein the first end is a distal end configured to retain a surgical tool for a minimally invasive surgical procedure and wherein the second end is a proximal end configured to be manipulated by a practitioner.

3. The robotic catheter of claim 2, wherein the torsional spring is configured to impart torque on the proximal end of the concentric tubes in a repeating pattern.

4. The robotic catheter of claim 1, wherein the first force is the same or substantially the same as the second force.

5. The robotic catheter of claim 1, wherein the first or second tube comprises a wall comprising silicon material.

6. A method of conducting a minimally invasive surgical procedure, comprising:
   with a robotic catheter comprising:
      a concentric arrangement of a first tube and a second tube arranged concentrically around the first tube, the first tube having a first bending resistance and a first torsional resistance, and the second tube having a second bending resistance and a second torsional resistance, wherein the robotic catheter is moveable between a first stable-equilibrium position and a second stable-equilibrium position, and wherein in the first stable-equilibrium position a first end of the robotic catheter applies a first force to a tissue and in the second stable-equilibrium position the first end applies a second force to the tissue; and
      a torsional spring positioned at a second end of the concentric arrangement of the first and second tubes and coupled with the second end of the concentric arrangement of the first and second tubes, such that, when the robotic catheter moves between the first stable-equilibrium position and the second stable-equilibrium position, the torsional spring causes the first and second tubes to counter-rotate relative to one another, causing the first end of the robotic catheter to transition between applying the first force and the second force;
   inserting the first end of the robotic catheter into a surgical site; and
   causing the first and second tubes to counter-rotate relative to one another to reposition the first end of the robotic catheter from the first stable-equilibrium position to the second stable-equilibrium position.

7. The method of claim 6, wherein moving the first end between the first stable-equilibrium position and the second stable-equilibrium position comprises synchronizing movement of the first end with movement of a patient's cardiac muscle.

8. The method of claim 6, wherein adjusting the position of the first end of the robotic catheter comprises imparting a pseudo-constant force on a patient's cardiac muscle.

9. A robotic catheter assembly, comprising:
   a first tube and a second tube arranged eccentrically relative to one another and coupled with a vertebra of a supportive spine, the vertebra at least partially surrounding the first and second tubes and coupled with the tubes via a plurality of bearings, the first tube having a first bending resistance and a first torsional resistance, and the second tube having a second bending resistance and a second torsional resistance;
   a plurality of gears coupled with a first end of the first and second tubes and configured to rotate the tubes; and
   a torsional spring coupled with the plurality of gears, such that, when the first tube and the second tube move between a first position and a second position, the torsional spring causes the first and second tubes to counter-rotate relative to one another causing a second end of the first and second tubes to apply a force to tissue.

10. The robotic catheter assembly of claim 9, wherein the first end is a proximal end configured to be manipulated by a practitioner and wherein the second end is a distal end configured to retain a surgical tool for a minimally invasive surgical procedure and.

11. The robotic catheter assembly of claim 10, wherein the torsional spring is configured to impart torque on the first end of the first and second tubes in a repeating pattern.

12. The robotic catheter assembly of claim 9, wherein the first or second tube comprises a wall comprising phantom silicon tissue.

13. A method of conducting a minimally invasive surgical procedure using the robotic catheter assembly of claim 9, the method comprising:
   inserting the second end of the robotic catheter into a surgical site;
   causing the first and second tubes to counter-rotate relative to one another to reposition the second end of the robotic catheter from a first stable-equilibrium position to a second stable-equilibrium position.

14. The method of claim 13, wherein moving the second end between the first stable-equilibrium position and the second stable-equilibrium position comprises synchronizing movement of the second end with movement of a patient's cardiac muscle.

15. The method of claim 13, wherein adjusting the position of the second end of the robotic catheter comprises imparting a pseudo-constant force on a patient's cardiac muscle.

* * * * *